(12) United States Patent
Ying et al.

(10) Patent No.: US 12,377,049 B2
(45) Date of Patent: Aug. 5, 2025

(54) FULVESTRANT PHARMACEUTICAL COMPOSITION, PREPARATION METHOD THEREFOR, AND APPLICATION THEREOF

(71) Applicant: SHANGHAI BOCIMED PHARMACEUTICAL CO., LTD., Shanghai (CN)

(72) Inventors: Shuhuan Ying, Shanghai (CN); Hong Li, Shanghai (CN); Zhixiang Chen, Shanghai (CN); Tingting Wang, Shanghai (CN)

(73) Assignee: SHANGHAI BOCIMED PHARMACEUTICAL CO., LTD., Shanghai (CN)

( * ) Notice: Subject to any disclaimer, the term of this patent is extended or adjusted under 35 U.S.C. 154(b) by 523 days.

(21) Appl. No.: 17/757,245

(22) PCT Filed: Dec. 10, 2020

(86) PCT No.: PCT/CN2020/135311
§ 371 (c)(1),
(2) Date: Jun. 13, 2022

(87) PCT Pub. No.: WO2021/115389
PCT Pub. Date: Jun. 17, 2021

(65) Prior Publication Data
US 2022/0370359 A1  Nov. 24, 2022

(30) Foreign Application Priority Data

Dec. 11, 2019 (CN) .......................... 201911262544.4
Jun. 24, 2020 (CN) .......................... 202010590154.6

(51) Int. Cl.
| | |
|---|---|
| *A61K 9/16* | (2006.01) |
| *A61K 9/00* | (2006.01) |
| *A61K 31/355* | (2006.01) |
| *A61K 31/375* | (2006.01) |
| *A61K 47/26* | (2006.01) |
| *A61K 47/44* | (2017.01) |
| *A61K 47/54* | (2017.01) |

(52) U.S. Cl.
CPC .......... *A61K 9/1641* (2013.01); *A61K 9/0019* (2013.01); *A61K 31/355* (2013.01); *A61K 31/375* (2013.01); *A61K 47/26* (2013.01); *A61K 47/44* (2013.01); *A61K 47/547* (2017.08)

(58) Field of Classification Search
CPC .. A61K 9/1641; A61K 9/0019; A61K 31/355; A61K 31/375; A61K 47/26; A61K 47/44; A61K 47/547; A61K 9/10; A61K 9/145; A61K 47/38; A61K 31/565; A61P 35/00
See application file for complete search history.

(56) References Cited

U.S. PATENT DOCUMENTS 6,774,122 B2    8/2004  Evans et al.

FOREIGN PATENT DOCUMENTS

| CN | 109310621 A | 2/2019 | |
|---|---|---|---|
| WO | 03006064 A1 | 1/2003 | |
| WO | 2012035516 A1 | 3/2012 | |
| WO | 2013182668 A1 | 12/2013 | |
| WO | WO-2017193048 A1 * | 11/2017 | ........... A61K 31/519 |
| WO | WO-2019094650 A1 * | 5/2019 | ........... A61K 31/519 |

* cited by examiner

*Primary Examiner* — Robert A Wax
*Assistant Examiner* — John Seungjai Kwon
(74) *Attorney, Agent, or Firm* — NKL Law; Allen Xue

(57) ABSTRACT

A fulvestrant pharmaceutical composition, a preparation method therefor, and an application thereof are provided. The fulvestrant pharmaceutical composition contains fulvestrant solid particles. The particle size of the fulvestrant solid particles satisfies that Dv(10) is selected from 0.400 micrometers to 6.000 micrometers, Dv(50) is selected from 0.700 micrometers to 6.000 micrometers, and Dv(90) is selected from 1.000 micrometers to 6.000 micrometers, provided that Dv(10) is not 0.400 micrometers, Dv(50) is not 0.700 micrometers, and Dv(90) is not 1.000 micrometers. The fulvestrant pharmaceutical composition has a long-acting sustained release.

10 Claims, 15 Drawing Sheets

FULVESTRANT PHARMACEUTICAL COMPOSITION, PREPARATION METHOD THEREFOR, AND APPLICATION THEREOF

CROSS-REFERENCE TO RELATED APPLICATIONS

This application is a U.S. national stage entry of PCT Application No. PCT/CN2020/135311, filed on Dec. 10, 2020, which claims priorities to Chinese Patent Application No. 201911262544.4, entitled "FULVESTRANT PHARMACEUTICAL COMPOSITION, PREPARATION METHOD THEREFOR AND APPLICATION THEREOF," filed before China National Intellectual Property Administration on Dec. 11, 2019, and Chinese Patent Application No. 202010590154.6, entitled "FULVESTRANT PHARMACEUTICAL COMPOSITION, PREPARATION METHOD THEREFOR AND APPLICATION THEREOF," filed before China National Intellectual Property Administration on Jun. 24, 2020, the content of which are incorporated herein by reference in their entireties.

TECHNICAL FIELD

The present disclosure belongs to the field of pharmaceuticals, and particularly relates to a fulvestrant pharmaceutical composition, and a preparation method therefor and use thereof.

BACKGROUND

Fulvestrant is a selective estrogen receptor degrader (SERD) for the treatment of hormone receptor-positive metastatic breast cancer in postmenopausal women whose disease has progressed after the anti-estrogen therapy. Fulvestrant has been approved by the FDA in 2002 for the treatment of hormone receptor-positive metastatic breast cancer.

Fulvestrant is chemically named 7-(9-(4,4,5,5,5-pentafluoropentylsulfinyl)nonyl)estra-1,3,5(10)-triene-3,17-diol and has a structure as shown in formula I:

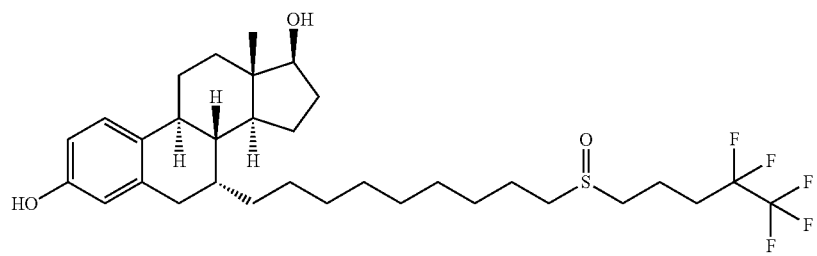

formula I

Fulvestrant is a lipophilic molecule with very low water solubility. Currently, fulvestrant is commonly administered by intramuscular injection of an oil-based fulvestrant formulation due to its poor solubility and low oral bioavailability. The current commercially available formulation of fulvestrant, FASLODEX™, is administered at 500 mg and requires two intramuscular administrations of a 5 mL injection prepared from a 50 mg/mL fulvestrant formulation. Each 5 mL injection contains 10 w/v % ethanol, 10 w/v % benzyl alcohol, and 15 w/v % benzyl benzoate as co-solvents, and is made up to 100 w/v % with castor oil as the other co-solvent and a release rate regulator. Since fulvestrant is dissolved with a viscous oil-based vehicle, the formulation is administered slowly (1-2 min per injection) and painfully. Warnings for injection pain, sciatica, neuropathic pain and peripheral neuropathy have been added to the label of FASLODEX™.

Therefore, it is a technical problem that needs to be solved urgently at present to find fulvestrant dosage forms with long-acting sustained release, convenient administration and low pain degree.

SUMMARY

The present disclosure aims to provide a fulvestrant pharmaceutical composition, a preparation method therefor and use thereof to solve the technical problems of non-ideal sustained release effect, inconvenient administration, high injection pain degree and the like of fulvestrant formulations in the prior art. The fulvestrant pharmaceutical composition of the present disclosure features long-acting sustained release and high bioavailability, is convenient to administer, reduces the administration volume, and greatly reduces the injection pain degree, thereby having a good marketing prospect.

The present disclosure provides a fulvestrant pharmaceutical composition comprising fulvestrant solid particles, wherein the fulvestrant solid particles have a particle size of Dv(10) selected from 0.400-6.000 μm, Dv(50) selected from 0.700-6000 μm and Dv(90) selected from 1.000-6.000 μm, provided that Dv(10) is not 0.400 μm, Dv(50) is not 0.700 μm, and Dv(90) is not 1.000 μm.

According to an embodiment of the present disclosure, the fulvestrant solid particles may have a particle size of Dv(10) of 0.500-6.000 μm, preferably 0.600-2.000 μm, and further preferably 0.900-1.800 μm, for example, 1.856 μm, 1.794 μm, 1.500 μm, 1.373 μm, 1.300 μm, 1,100 μm, 1.058 μm, 1.010 μm, 1.000 μm, 0.920 μm, 0.910 μm, 0.903 μm or 0.806 μm.

According to an embodiment of the present disclosure, the fulvestrant solid particles may have a particle size of Dv(50) of 0.800-6.000 μm, preferably 0.900-4.000 μm, and further preferably 1.000-3.000 μm, for example, Dv(50) of 4.215 μm, 2.939 μm, 2.610 μm, 2.500 μm, 1.983 μm, 1.887 μm, 1.500 μm, 1.493 μm, 1.241 μm, 1.202 μm or 1.127 μm.

According to an embodiment of the present disclosure, the fulvestrant solid particles may have a particle size of Dv(90) of 1.000-5.000 μm, preferably 1.500-4.500 μm, for example, 4.279 μm, 4.000 μm, 3.644 μm, 3.500 μm, 3.027 μm, 2.500 μm, 2.058 μm, 2.000 μm, 1.955 μm, 1.644 μm or 1,587 μm.

According to an embodiment of the present disclosure, the fulvestrant solid particles may have a particle size of Dv(25) of 1.000-3.000 μm, for example, 2.284 μm, 1.840 μm, 1.376 μm, 1.270 μm, 1.235 μm, 1.056 μm, 1.075 μm or 0.922 μm.

According to an embodiment of the present disclosure, the fulvestrant solid particles may have a particle size of Dv(75) of 1.000-4.000 μm, for example, 3.781 μm, 3.680 μm, 2.823 μm, 2.463 μm, 1.795 μm, 1.469 μm, 1.459 μm or 1.397 μm.

According to an embodiment of the present disclosure, the fulvestrant pharmaceutical composition may further comprise a vehicle. The vehicle may be an oily vehicle and/or a non-oily vehicle. The oily vehicle comprises, but is not limited to one or more of castor oil, triglyceride, cottonseed oil, sesame oil, and the like.

The non-oily vehicle comprises, but is not limited to water. The water may be conventional commercially available water for injection, and is preferably sterile water for injection.

According to an embodiment of the present disclosure, the fulvestrant pharmaceutical composition may further comprise one or more selected from the following: a suspending agent, a wetting agent, a osmotic pressure regulator, a solvent, a stabilizer, a buffer, a pH adjusting agent, a surfactant, a polymer, an electrolyte, a non-electrolyte, and a co-solvent, wherein the polymer may be a cross-linked polymer and/or a non-cross-linked polymer.

According to an embodiment of the present disclosure, the suspending agent comprises, but is not limited to one or more of sodium carboxymethylcellulose, polyethylene glycol and povidone.

According to an embodiment of the present disclosure, the wetting agent comprises, but is not limited to one or more of poloxamer and tween. The tween may be a conventional commercially available tween reagent, such as tween 20 and/or tween 80.

According to an embodiment of the present disclosure, the osmotic pressure regulator comprises, but is not limited to one or more of sodium chloride, mannitol and sucrose.

According to an embodiment of the present disclosure, the solvent comprises, but is not limited to one or more of water for injection and oil for injection. For example, the oil for injection comprises, but is not limited to medium-chain triglyceride (MCT). For example, the water for injection may be conventional commercially available water for injection, and is preferably sterile water for injection.

According to an embodiment of the present disclosure, the stabilizer comprises, but is not limited to one or more of an antioxidant, a metal ion chelating agent, polyethylene oxide (PEO), polyethylene oxide derivatives, polysorbate, poloxamer, polyethoxylated vegetable oil, polyethoxylated castor oil, sorbitan palmitate, lecithin, polyvinyl alcohol, human serum albumin, polyvinylpyrrolidone, povidone, polyethylene glycol, sodium chloride, calcium chloride, dextrose, glycerol, mannitol, and a cross-linked polymer. For example, the antioxidant comprises, but is not limited to one or more of citric acid, vitamin C and vitamin E. For example, the metal ion chelating agent comprises, but is not limited to ethylenediaminetetraacetic acid (EDTA). For example, the poloxamer comprises, but is not limited to one or more of poloxamer 188, poloxamer 124 and poloxamer 407. For example, the polysorbate comprises, but is not limited to one or more of polysorbate 80 and polysorbate 20. For example, the povidone comprises, but is not limited to one or more of povidone K12, povidone K17, PLASDONE™ C-12 povidone, PLASDONE™ C-17 povidone, and PLASDONE™ C-30 povidone. For example, the polyethylene glycol comprises, but is not limited to polyethylene glycol 3350.

According to an embodiment of the present disclosure, the cross-linked polymer comprises, but is not limited to sodium carboxymethylcellulose.

According to an embodiment of the present disclosure, the buffer comprises, but is not limited to one of or a mixture of two or more of phosphoric acid, phosphate, citric acid, sodium citrate, hydrochloric acid, sodium hydroxide, sodium citrate, citric acid, and tris(hydroxymethyl)aminomethane (Tris).

According to an embodiment of the present disclosure, the pH adjusting agent comprises, but is not limited to one or more of phosphoric acid, phosphate, citric acid, sodium citrate, hydrochloric acid and sodium hydroxide.

According to an embodiment of the present disclosure, the phosphate comprises, but is not limited to one or more of disodium hydrogen phosphate monohydrate ($Na_2HPO_4 \cdot H_2O$), disodium hydrogen phosphate dihydrate ($Na_2HPO_4 \cdot 2H_2O$), anhydrous disodium hydrogen phosphate (anhydrous $Na_2HPO_4$), sodium dihydrogen phosphate monohydrate ($NaH_2PO_4 \cdot H_2O$), sodium dihydrogen phosphate dihydrate ($NaH_2PO_4 \cdot 2H_2O$), and anhydrous sodium dihydrogen phosphate (anhydrous $NaH_2PO_4$).

According to an embodiment of the present disclosure, the co-solvent comprises, but is not limited to one or more of ethanol and propylene glycol.

According to an embodiment of the present disclosure, the fulvestrant solid particles in the fulvestrant pharmaceutical composition have a weight fraction of 1.00%-50.00%, preferably 10.00%-40.00%, for example, 18.09%, 19.59%, 24.66% or 25.00%, wherein the weight fraction refers to the percentage of the weight of the fulvestrant solid particles to the total weight of the fulvestrant pharmaceutical composition.

According to an embodiment of the present disclosure, the wetting agent in the fulvestrant pharmaceutical composition has a weight fraction of 0-5.00%, preferably 1.00%-3.00%, for example, 1.67%, 1.62% or 1.74%, wherein the weight fraction refers to the percentage of the weight of the wetting agent to the total weight of the fulvestrant pharmaceutical composition.

According to an embodiment of the present disclosure, the suspending agent in the fulvestrant pharmaceutical composition has a weight fraction of 0-5.00%, preferably 1.00%-3.00%, for example, 0.20% or 1.00%, wherein the weight fraction refers to the percentage of the weight of the suspending agent to the total weight of the fulvestrant pharmaceutical composition.

According to an embodiment of the present disclosure, the osmotic pressure regulator in the fulvestrant pharmaceutical composition has a weight fraction of 0-5.00%, preferably 1.00%-3.00%, for example, 2.29%, 2.82% or 2.89%, wherein the weight fraction refers to the percentage of the weight of the osmotic pressure regulator to the total weight of the fulvestrant pharmaceutical composition.

According to an embodiment of the present disclosure, the buffer in the fulvestrant pharmaceutical composition has a weight fraction of 0-1.00%, preferably 0.20%-0.80%, for example, 0.42%, 0.43% or 0.51%, wherein the weight fraction refers to the percentage of the weight of the buffer to the total weight of the fulvestrant pharmaceutical composition.

According to an embodiment of the present disclosure, the pH adjusting agent in the fulvestrant pharmaceutical composition is preferably used in an amount to adjust the pH of the composition solution to 6.5-8.0, for example, 7.4.

According to an embodiment of the present disclosure, the fulvestrant pharmaceutical composition preferably comprises the following components: 1.00-50.00% fulvestrant solid particles, 0-5.00% wetting agent, 0-5.00% suspending agent, 0-5.00% osmotic pressure regulator, and 0-1.00% buffer and solvent.

According to an embodiment of the present disclosure, the fulvestrant pharmaceutical composition may be selected from any of the following formulas:
formula I: 18.09% fulvestrant solid particles, 1.67% wetting agent and 80.24% water;
formula II: 19.59% fulvestrant solid particles, 1.74% wetting agent and 78.67% water;
formula III: 24.66% fulvestrant solid particles, 1.62% wetting agent, 1.00% suspending agent, 2.82% osmotic pressure regulator, 0.42% buffer and 0-1% pH adjusting agent, wherein preferably, the rest is water;
formula IV: 25.00% fulvestrant solid particles, 1.62% wetting agent, 1.00% suspending agent, 189% osmotic pressure regulator, 0.43% buffer and 0-1% pH adjusting agent, wherein preferably, the rest is water; and
formula V: 25.00% fulvestrant solid particles, 1.62% wetting, 0.20% suspending agent, 2.29% osmotic pressure regulator, 0.51% buffer and 70.38% water.

According to an embodiment of the present disclosure, the fulvestrant pharmaceutical composition may also be selected from any one of the following formulas:
formula A: 18.09% fulvestrant solid particles, 1.67% tween 80 and 80.24% sterile water for injection;
formula B: 19.59% fulvestrant solid particles, 1.74% tween 80 and 78.67% sterile water for injection;
formula C: 24.66% fulvestrant solid particles, 1.62% tween 20, 1.00% sodium carboxymethyl cellulose, 2.82% mannitol, 0.42% anhydrous sodium dihydrogen phosphate, sodium hydroxide and sterile water for injection, wherein preferably, the fulvestrant pharmaceutical composition has a pH of 7.4;
formula D: 25.00% fulvestrant solid particles, 1.62% tween 20, 1.00% sodium carboxymethylcellulose, 2.89% mannitol, 0.43% anhydrous sodium dihydrogen phosphate, sodium hydroxide and sterile water for injection, wherein preferably, the fulvestrant pharmaceutical composition has a pH of 7.4; and
formula E: 25.00% fulvestrant solid particles, 1.62% tween 20, 0.20% sodium carboxymethylcellulose, 2.29% mannitol, 0.09% anhydrous sodium dihydrogen phosphate, 0.42% anhydrous disodium hydrogen phosphate and 70.38% sterile water for injection.

The present disclosure also provides a preparation method for the fulvestrant pharmaceutical composition, which comprises the following steps:
step 1: mixing the fulvestrant solid particles with other components in the formula to obtain a premix; and
step 2: grinding the premix obtained in the step 1 together with zirconium beads or jet milling the premix obtained in the step 1, so as to obtain the fulvestrant pharmaceutical composition.

According to an embodiment of the present disclosure, in the step 1, the mixing is preferably mixing by stirring.

According to an embodiment of the present disclosure, in the step 2, the zirconium beads may have a particle size of 0.01-2 mm, for example, 0.3 mm, 0.6 mm or 1 mm.

According to an embodiment of the present disclosure, in the step 2, the zirconium beads and the premix are in a volume ratio of 1-5, for example, 1, 1.5, 2 or 3.

According to an embodiment of the present disclosure, in the step 2, the grinding may be performed for 1 min to 10 h, or 5 min to 8 h, for example, 7 min, 4 h, 7 h or 8 h.

According to an embodiment of the present disclosure, the zirconium beads are conventional commercially available zirconium oxide beads.

The present disclosure also provides use of the fulvestrant pharmaceutical composition in the manufacture of a fulvestrant pharmaceutical formulation.

According to an embodiment of the present disclosure, the fulvestrant pharmaceutical formulation comprises, but is not limited to one or more of a tablet, a granule, a capsule, a pellet, an oral liquid, an injection and the like. Preferably, the tablet comprises, but is not limited to one or more of a sustained-release tablet, an osmotic pump tablet and an orally disintegrating tablet. Preferably, the injection may be a liquid injection, a powder for injection or a tablet for injection; for example, the liquid injection may be a suspension, such as an aqueous suspension or an oily suspension; for example, the powder for injection is a freeze-dried powder injection.

According to an embodiment of the present disclosure, the injection may be a long-acting injection, wherein the long-acting injection may be either an aqueous suspension or an oily suspension, or a powder for injection that will be dispersed into a suspension with a specific diluent when in use.

According to an embodiment of the present disclosure, the long-acting injection has fulvestrant at a concentration of no less than 50 mg/mL, for example, not less than 100 mg/mL, preferably 120-400 mg/mL, illustratively 200 mg/mL, 250 mg/mL, 263.8 mg/mL, 270.1 mg/mL, 300 mg/mL or 341.9 mg/mL.

The present disclosure also provides a fulvestrant pharmaceutical formulation comprising the fulvestrant pharmaceutical composition.

According to an embodiment of the present disclosure, the fulvestrant pharmaceutical formulation has a dosage form selection and/or fulvestrant concentration as described above.

The present disclosure also provides use of the fulvestrant pharmaceutical composition and/or fulvestrant pharmaceutical formulation in the prevention and/or treatment of hormone receptor-positive metastatic breast cancer.

The present disclosure also provides a method for preventing and/or treating hormone receptor-positive metastatic breast cancer, which comprises administering the fulvestrant pharmaceutical composition and/or fulvestrant pharmaceutical formulation to a patient, e.g., a human in need thereof.

According to the present disclosure, the terms "Dv(10)", "Dv(25)", "Dv(50)", "Dv(75)" and "Dv(90)" refer to the particle diameter weighted by volume, wherein a cumulative of 10 v/v %, 25 v/v %, 50 v/v %, 75 v/v % or 90 v/v % of the particles have equal or smaller diameters in the measurement. For example, if the Dv(50) of a population of particles is about 25 μm, it means that 50% by volume of the particles have a diameter less than or equal to about 25 μm. The terms "Dn (10)", "Dn (25)", "Dn (50)", "Dn (75)" and "Dn (90)" refer to the particle diameter weighted by number, wherein a cumulative of 10%, 25%, 50%, 75% or 90% of the particles have equal or smaller diameters in the measurement. For example, if the Dn (50) of a population of particles is about 25 μm, it means that 50% by number of the particles have a diameter less than or equal to about 25 μm.

The above preferred conditions may be combined arbitrarily to obtain preferred embodiments of the present disclosure without departing from the general knowledge in the art.

The reagents and starting materials used in the present disclosure are commercially available.

According to an embodiment of the present disclosure, the room temperature is an environment temperature of 10-35° C.

Beneficial effects of the present disclosure: the fulvestrant pharmaceutical composition features long-acting sustained release and high bioavailability, is convenient to administer, reduces the administration volume, and greatly reduces the injection pain degree, thereby having a good marketing prospect.

BRIEF DESCRIPTION OF THE DRAWINGS

FIG. 27 shows pharmacokinetic profiles of fulvestrant in formulation No. 3 of Example 11; wherein

Figure 1:
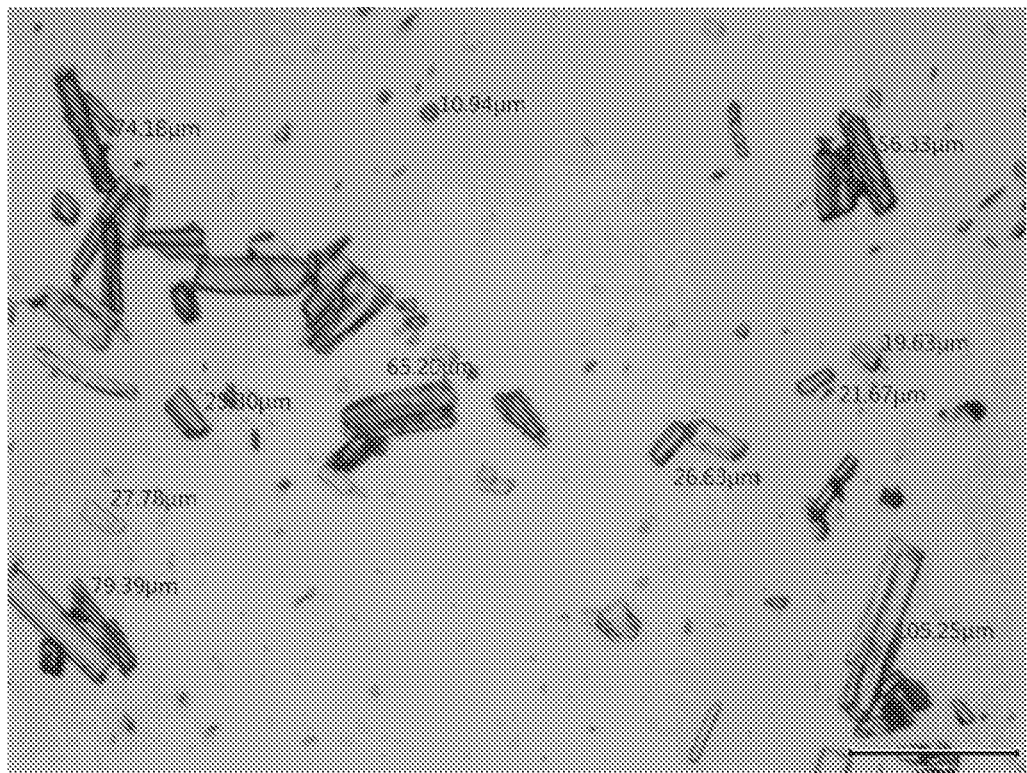
FIG. 1 shows a particle size morphology of the fulvestrant solid particles before grinding in Example 1, on a 100 μm scale.
Figure 28:
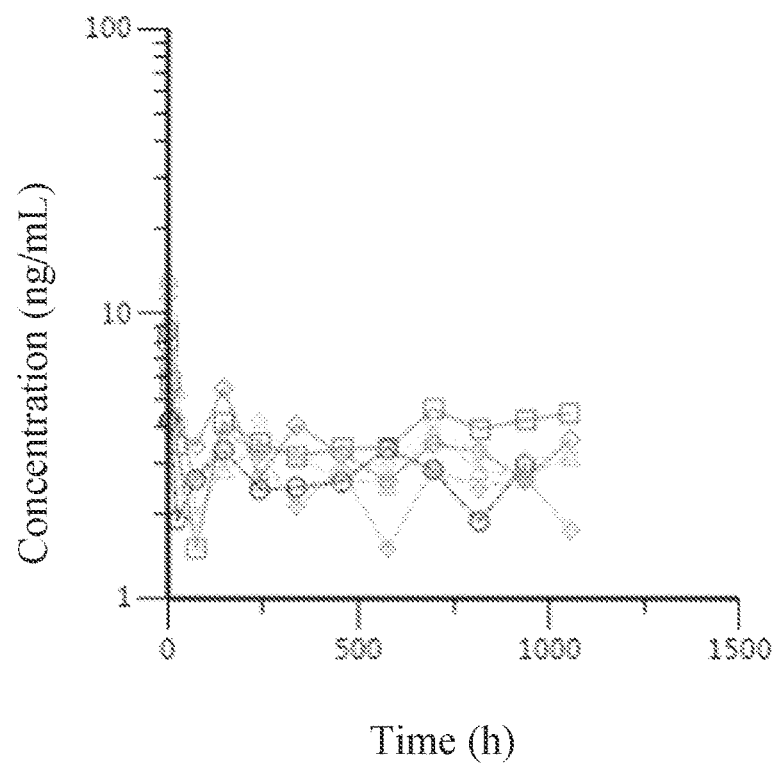

- represents the pharmacokinetic profile in animal 1;
- represents the pharmacokinetic profile in animal 2;
- represents the pharmacokinetic profile in animal 3;
- represents the pharmacokinetic profile in animal 4;
- represents the pharmacokinetic profile in animal 5; and
- represents the pharmacokinetic profile in animal 6;

FIG. 28 shows pharmacokinetic profiles of fulvestrant in formulation No. 4 of Example 11; wherein

Figure 29:
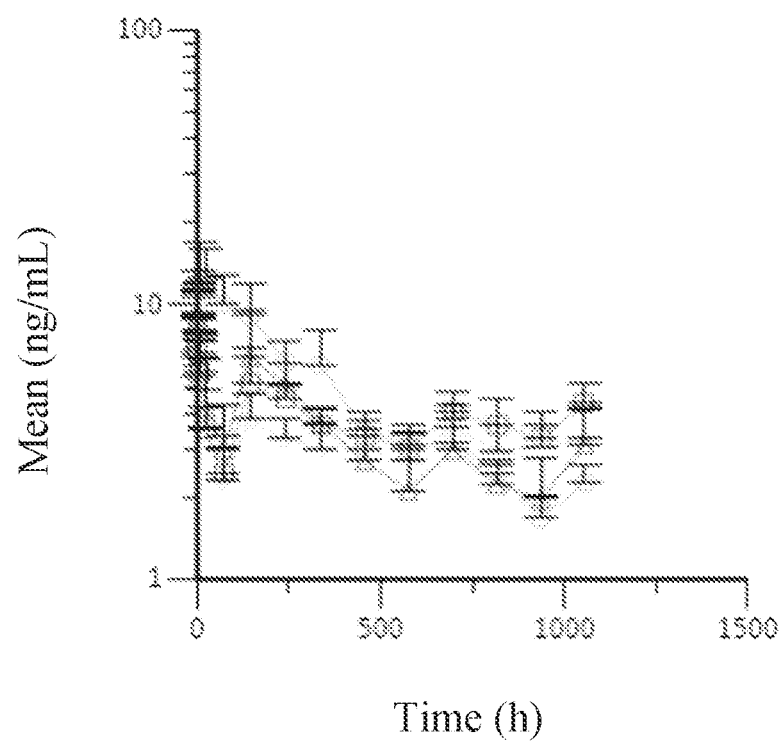

- represents the pharmacokinetic profile in animal 1;
- represents the pharmacokinetic profile in animal 2;
- represents the pharmacokinetic profile in animal 3;
- represents the pharmacokinetic profile in animal 4;
- represents the pharmacokinetic profile in animal 5; and
- represents the pharmacokinetic profile in animal 6; and FIG. 29 shows mean pharmacokinetic profiles of fulvestrant in formulation No. 1 i.e. the marketed comparative fulvestrant formulation) and formulation Nos. 2, 3 and 4; wherein

- represents the mean pharmacokinetic profile of fulvestrant in formulation No. 1;
- represents the mean pharmacokinetic profile of fulvestrant in formulation No. 2;
- represents the mean pharmacokinetic profile of fulvestrant in formulation No. 3; and
- represents the mean pharmacokinetic profile of fulvestrant in formulation No. 4.

DETAILED DESCRIPTION

The technical scheme of the present disclosure will be further illustrated in detail with reference to the following specific examples. It should be understood that the following examples are merely exemplary illustration and explanation of the present disclosure, and should not be construed as limiting the protection scope of the present disclosure. All techniques implemented based on the above contents of the present disclosure are encompassed within the protection scope of the present disclosure.

Unless otherwise stated, the starting materials and reagents used in the following examples are all commercially available products or can be prepared by known methods.

Unless otherwise specified, the particle sizes described in the following examples are all particle sizes Dv weighted by volume.

Example 1

TABLE 1

| Formula of the suspension injection of Example 1 | | |
|---|---|---|
| Component | Ratio (%, W/W) | Feeding amount (g) |
| Fulvestrant | 18.09 | 1.94 |
| Tween 80 | 1.67 | 0.18 |

TABLE 1-continued

| Formula of the suspension injection of Example 1 | | |
|---|---|---|
| Component | Ratio (%, W/W) | Feeding amount (g) |
| Sterile water for injection | 80.24 | 8.60 |

According to the formula as shown in Table 1, 0.18 g of tween 80 was weighed, and 1.94 g of fulvestrant solid particles were added, followed by the addition of 8.60 g of sterile water for injection, and the mixture was stirred and mixed well to obtain a premixed solution.

The premixed solution and 118.5 g of 1 mm zirconium beads were added into a grinding jar (the volume ratio of the premixed solution to the zirconium beads is 1:3) for grinding to obtain the fulvestrant pharmaceutical composition as a suspension injection. The grinding was performed in a ball mill, and the parameters of the planetary ball mill were set as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min.

Figure 2:
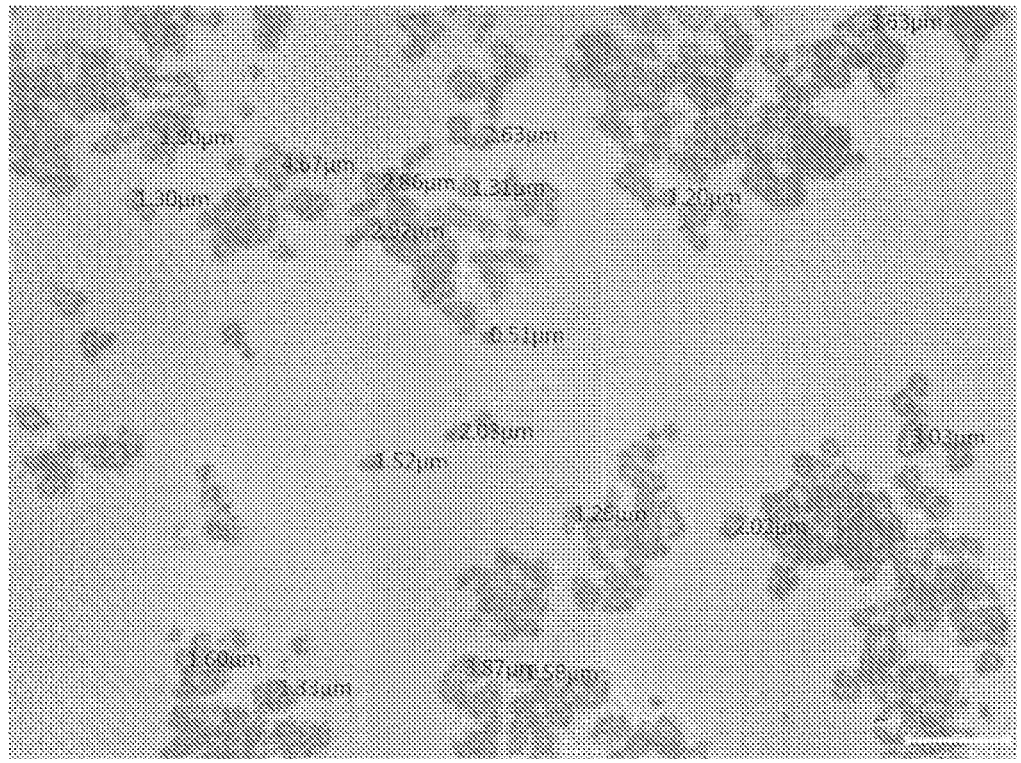
FIG. 2 shows a particle size morphology of the fulvestrant solid particles after grinding for 5 min in Example 1, on a 10 μm scale.
Figure 3:
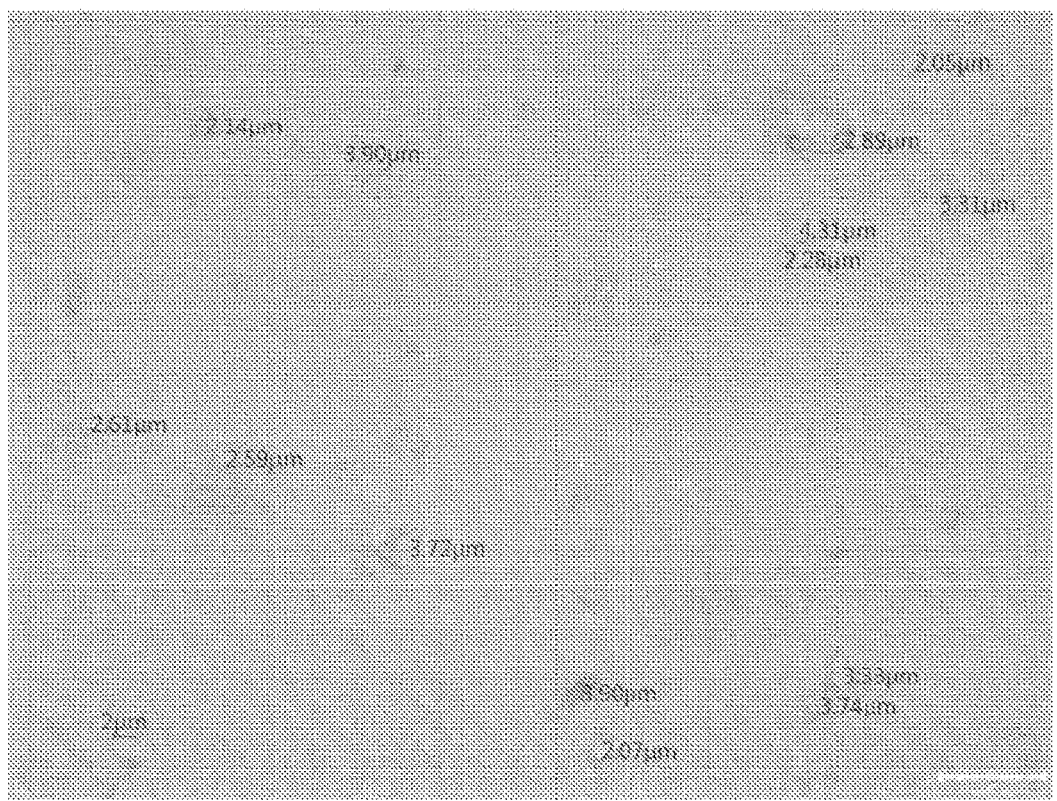
FIG. 3 shows a particle size morphology of the fulvestrant solid particles after grinding for 7 min in Example 1, on a 10 μm scale.

After the determination using a laser particle analyzer (the parameters were set as follows: the dispersion medium: water, the refractive index of the dispersion medium: 1.333, the absorbance of the sample material: 0.01, and the refractive index of the sample material: 1.521), the particle size distribution of the fulvestrant solid particles in the suspension is shown in Table 2. The particle size morphology of the fulvestrant solid particles in the suspension before grinding is shown in FIG. 1, the particle size morphology of the fulvestrant solid particles after grinding for 5 min is shown in FIG. 2, and the particle size morphology of the fulvestrant solid particles after grinding for 7 min is shown in FIG. 3.

TABLE 2

| Particle size distribution of fulvestrant in the suspension of Example 1 | | | | | |
|---|---|---|---|---|---|
| No. | D10 (μm) | D25 (μm) | D50 (μm) | D75 (μm) | D90 (μm) |
| Example 1 | 1.794 | 2.284 | 2.939 | 3.68 | 4.279 |

Example 2

TABLE 3

| Formula of the suspension injection of Example 2 | | |
|---|---|---|
| Component | Ratio (%, W/W) | Feeding amount (g) |
| Fulvestrant | 19.59 | 0.98 |
| Tween 80 | 1.74 | 0.09 |
| Sterile water for injection | 78.67 | 3.94 |

According to the formula as shown in Table 3, 0.09 g of tween 80 was weighed, and 0.98 g of fulvestrant solid particles were added, followed by the addition of 3.94 g of sterile water for injection, and the mixture was stirred and mixed well to obtain a premixed solution.

The premixed solution and 60.00 g of 1 mm zirconium beads were added into a grinding jar (the volume ratio of the premixed solution to the zirconium beads is 1:3) for grinding for 7 h to obtain the fulvestrant pharmaceutical composition as a suspension injection. The grinding was performed in a ball mill, and the parameters of the planetary ball mill were set as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min.

Figure 4:
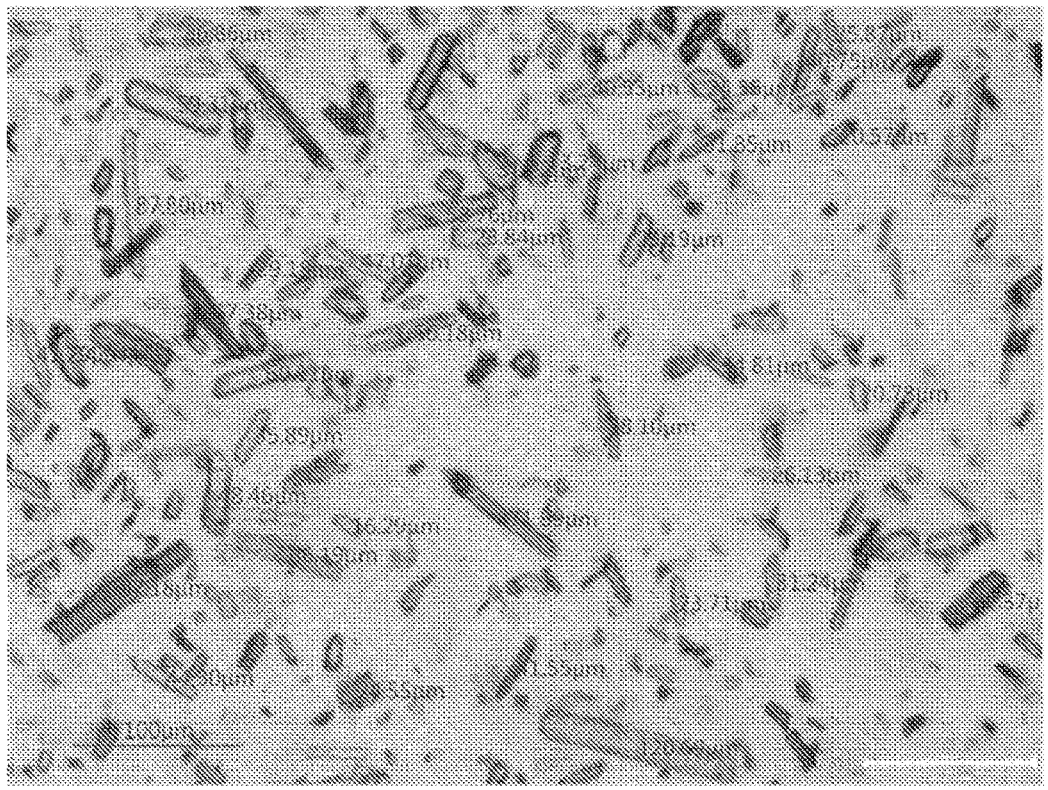
FIG. 4 shows a particle size morphology of the fulvestrant solid particles before grinding in Example 2, on a 100 μm scale.
Figure 5:
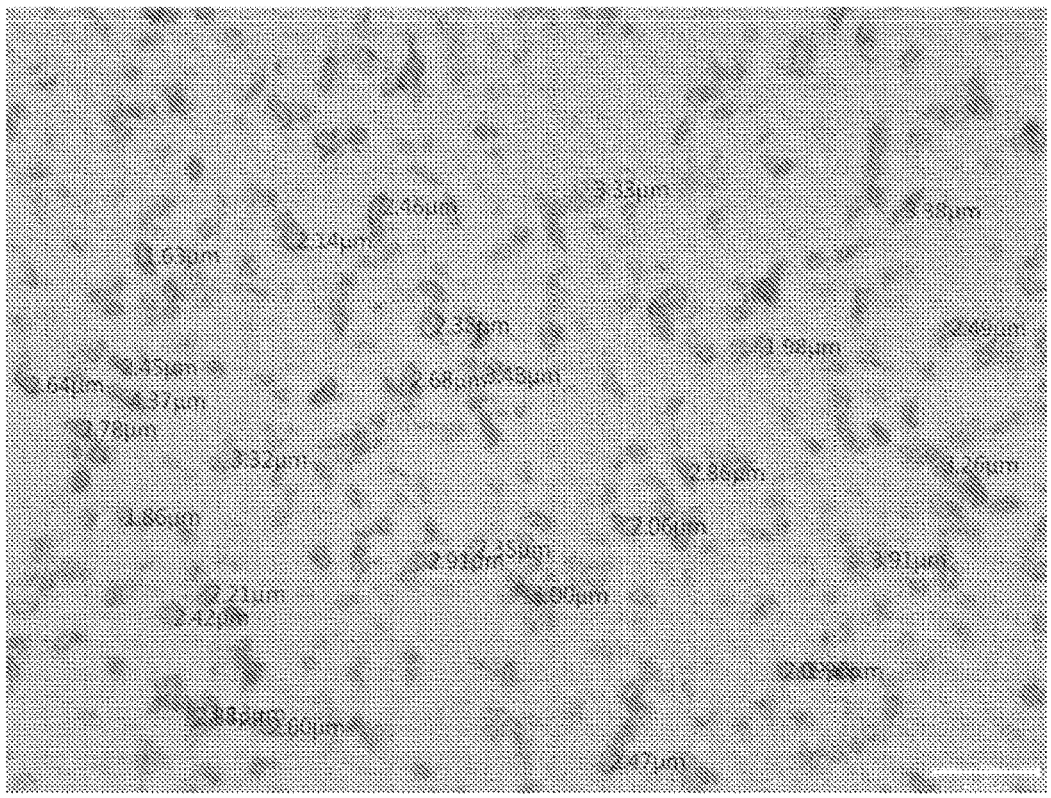
FIG. 5 shows a particle size morphology of the fulvestrant solid particles after grinding for 30 min in Example 2, on a 10 μm scale.
Figure 6:
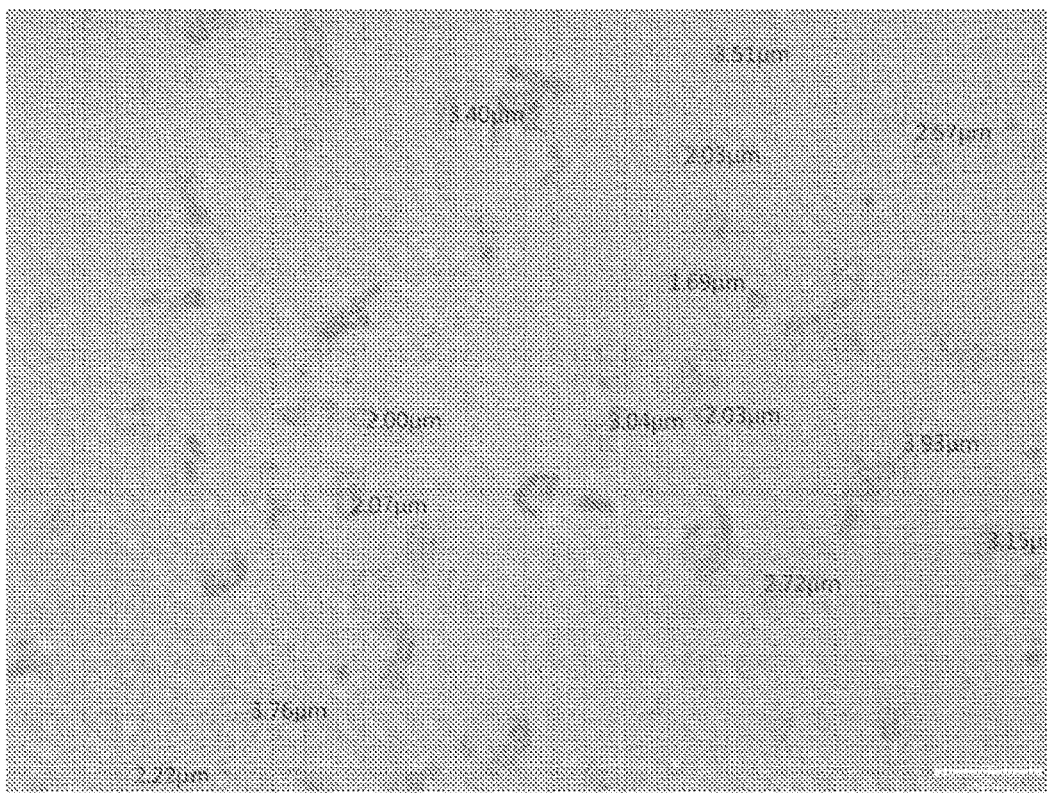
FIG. 6 shows a particle size morphology of the fulvestrant solid particles after grinding for 1 h in Example 2, on a 10 μm scale.
Figure 7:
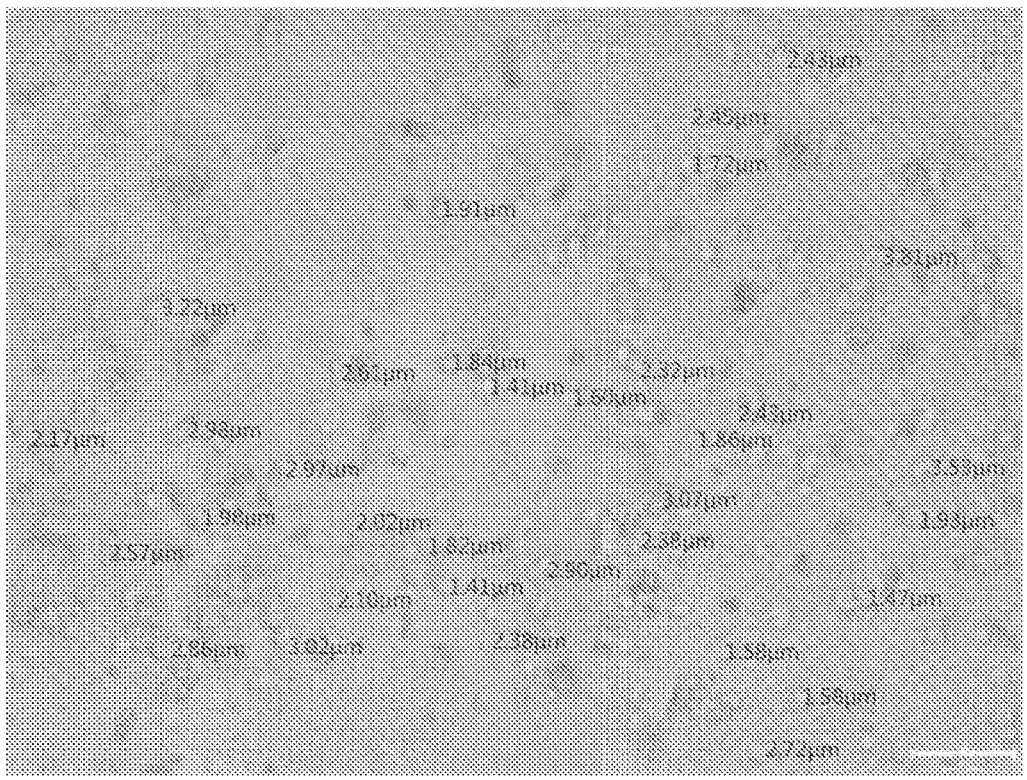
FIG. 7 shows a particle size morphology of the fulvestrant solid particles after grinding for 2 h in Example 2, on a 10 μm scale.
Figure 8:
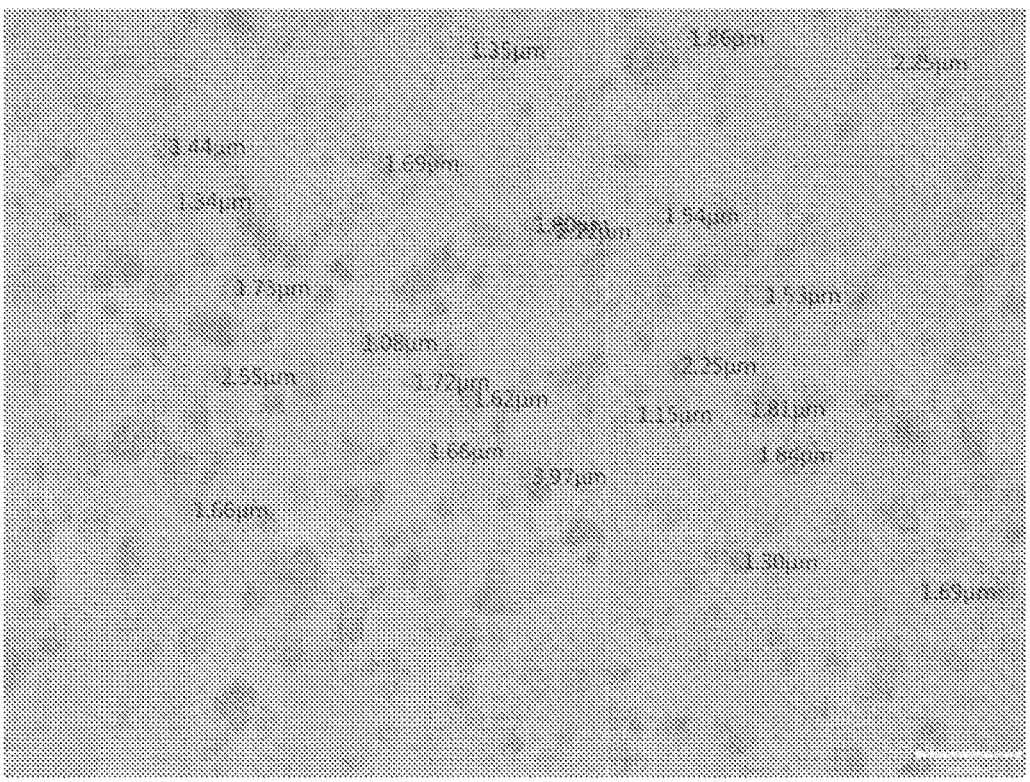
FIG. 8 shows a particle size morphology of the fulvestrant solid particles after grinding for 4 h in Example 2, on a 10 μm scale.

After the determination using a laser particle analyzer (the parameters were set as follows: the dispersion medium: water, the refractive index of the dispersion medium: 1.333, the absorbance of the sample material: 0.01, and the refractive index of the sample material: 1.521), the particle size distribution of the fulvestrant solid particles in the suspension after grinding for different periods of time is shown in Table 4. The particle size morphology of the fulvestrant solid particles in the suspension before grinding is shown in FIG. 4, the particle size morphology of the fulvestrant solid particles after grinding for 30 min is shown in FIG. 5, the particle size morphology of the fulvestrant solid particles after grinding for 1 h is shown in FIG. 6, the particle size morphology of the fulvestrant solid particles after grinding for 2 h is shown in FIG. 7, and the particle size morphology of the fulvestrant solid particles after grinding for 4 h is shown in FIG. 8.

TABLE 4

Particle size distribution of fulvestrant in the suspension of Example 2

| Grinding time | D10 (μm) | D25 (μm) | D50 (μm) | D75 (μm) | D90 (μm) |
|---|---|---|---|---|---|
| 1 hr | 1.215 | 1.764 | 2.468 | 3.238 | 4.012 |
| 4 hrs | 1.010 | 1.376 | 1.887 | 2.463 | 3.027 |

Example 3

TABLE 5

Formula of the suspension injection of Example 3

| Component | Ratio (%, W/W) | Feeding amount (g) |
|---|---|---|
| Fulvestrant | 24.66 | 7.51 |
| Tween 20 | 1.62 | 0.492 |
| Sodium carboxymethylcellulose | 1.00 | 0.30 |
| Mannitol | 2.82 | 22.00 |
| Anhydrous sodium dihydrogen phosphate | 0.42 | |
| Sodium hydroxide | q.s. to pH 7.4 | |
| Sterile water for injection | q.s. to 100 | |

According to the formula as shown in Table 5, 0.492 g of tween 20 was weighed, and 7.51 g of fulvestrant solid particles were added, followed by the addition of 4% mannitol-pH 7.4 anhydrous sodium dihydrogen phosphate solution to make up to 30 g (the percentage here refers to the percentage of the mass of mannitol to the total volume of mannitol-pH 7.4 anhydrous sodium dihydrogen phosphate solution), and the mixture was stirred and mixed well to obtain a premixed solution.

The premixed solution and 97.6 g of 0.3 mm zirconium beads were added into a grinding jar (the volume ratio of the premixed solution to the zirconium beads is 1:1) for grinding for 3 h to obtain the fulvestrant pharmaceutical composition as a suspension injection. The grinding was performed in a ball mill, and the parameters of the planetary ball mill were set as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min.

After the determination using a laser particle analyzer (the parameters were set as follows: the dispersion medium: water, the refractive index of the dispersion medium: 1.333, the absorbance of the sample material: 0.01, and the refractive index of the sample material: 1.521), the particle size distribution of the fulvestrant solid particles in the suspension after grinding for different periods of time is shown in Table 6. After grinding, 0.30 g of CMC-Na (sodium carboxymethylcellulose) was added and the mixture was fully stirred and mixed well. The sample was taken out and filtered to remove the grinding beads. The filtrate was subpackaged into vials and capped, placed in aluminum foil packages and stored at 4° C. away from the light.

TABLE 6

Particle size distribution of fulvestrant in the suspension of Example 3

| Grinding time | D10 (μm) | D25 (μm) | D50 (μm) | D75 (μm) | D90 (μm) |
|---|---|---|---|---|---|
| 0 min | 5.837 | 11.177 | 20.476 | 39.125 | 83.029 |
| 10 min | 1.315 | 1.75 | 2.327 | 2.99 | 3.639 |
| 1 hr | 1.054 | 1.457 | 2.051 | 2.664 | 3.254 |
| 4 hrs | 0.903 | 1.27 | 1.983 | 2.823 | 3.644 |

Stability Test on the Fulvestrant Suspensions Prepared in Examples 1-3

The fulvestrant suspensions prepared in Examples 1 and 2 were stored in a refrigerator at 4° C. for 14 days or 10 days, and tested for related substances. The results are shown in Table 7.

Figure 9:
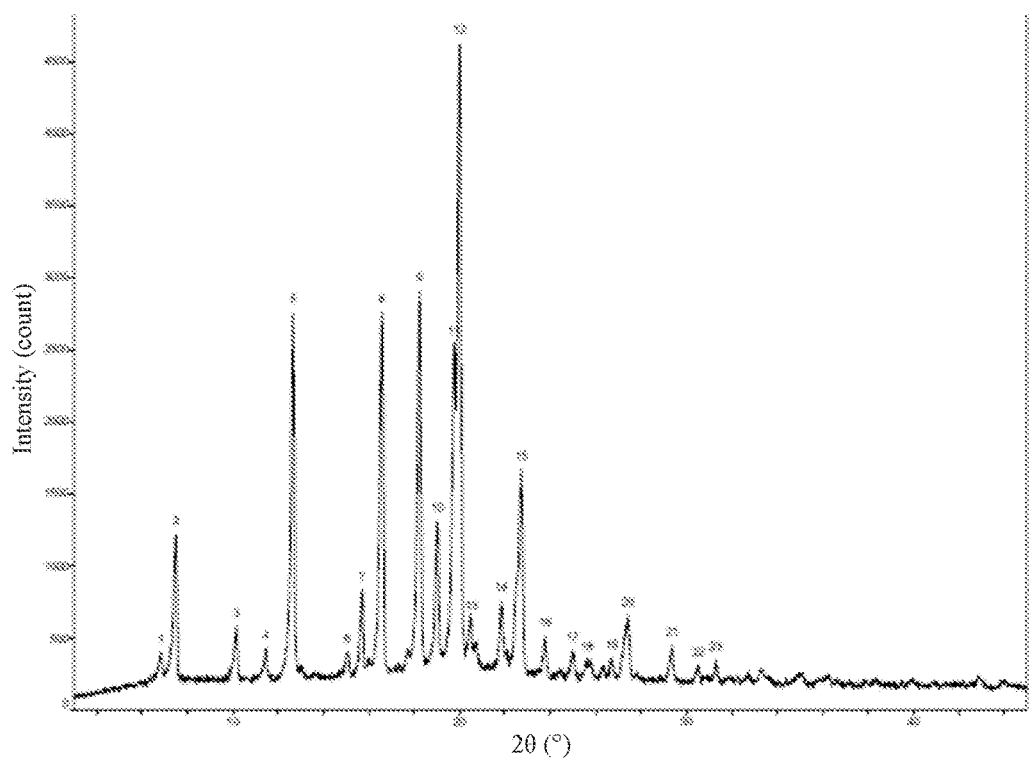
FIG. 9 shows an XRPD pattern of the fulvestrant solid particles before grinding in Example 3, wherein instrument model is Bruker D8 Advance X-ray diffractometer, and test condition is Target: Cu 40 kv 40 mA.
Figure 10:
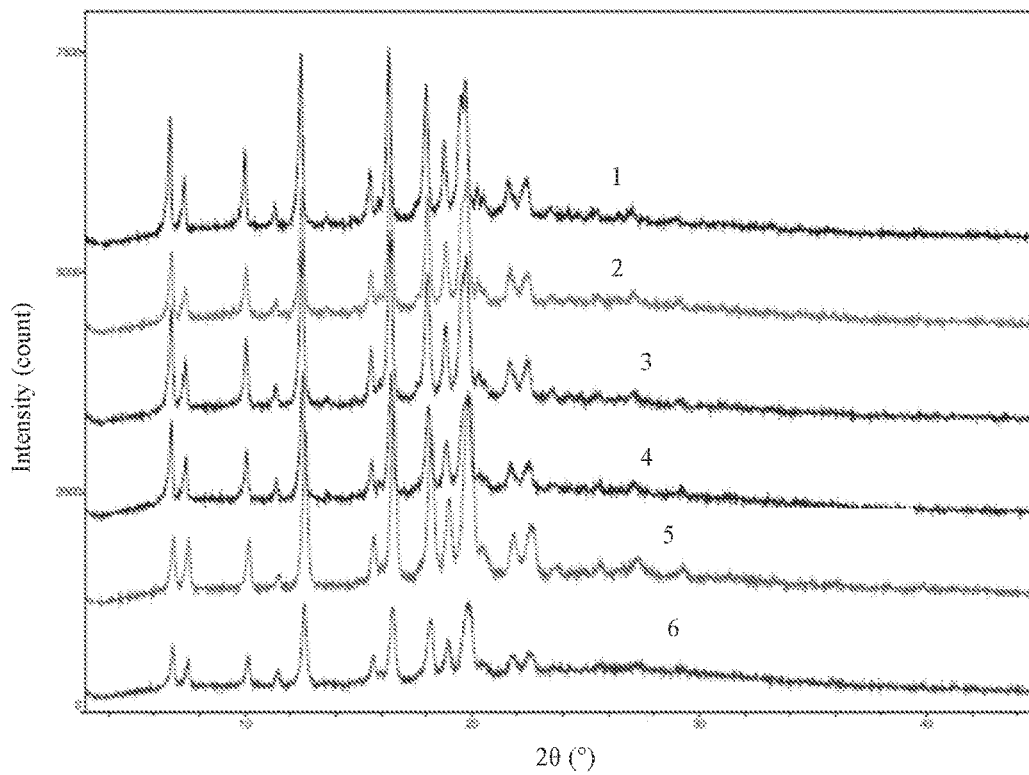
FIG. 10 shows XRPD patterns of the fulvestrant solid particles in the suspensions after grinding in Example 3 after being placed at 60° C. for 20 days, at 40° C. for 20 days, at 40° C. for 30 days, at 25° C. for 30 days, at 4° C. for 30 days and at −20° C. for 30 days, respectively; wherein,
1 represents the XRPD pattern of the fulvestrant solid particles in the suspension after grinding in Example 3 after being placed at 60° C. for 20 days;
2 represents the XRPD pattern of the fulvestrant solid particles in the suspension after grinding in Example 3 after being placed at 40° C. for 30 days;
3 represents the XRPD pattern of the fulvestrant solid particles in the suspension after grinding in Example 3 after being placed at 40° C. for 20 days;
4 represents the XRPD pattern of the fulvestrant solid particles in the suspension after grinding in Example 3 after being placed at 25° C. for 30 days;
5 represents the XRPD pattern of the fulvestrant solid particles in the suspension after grinding in Example 3 after being placed at 4° C. for 30 days; and
6 represents the XRPD pattern of the fulvestrant solid particles in the suspension after grinding in Example 3 after being placed at −20° C. for 30 days.
Figure 11:
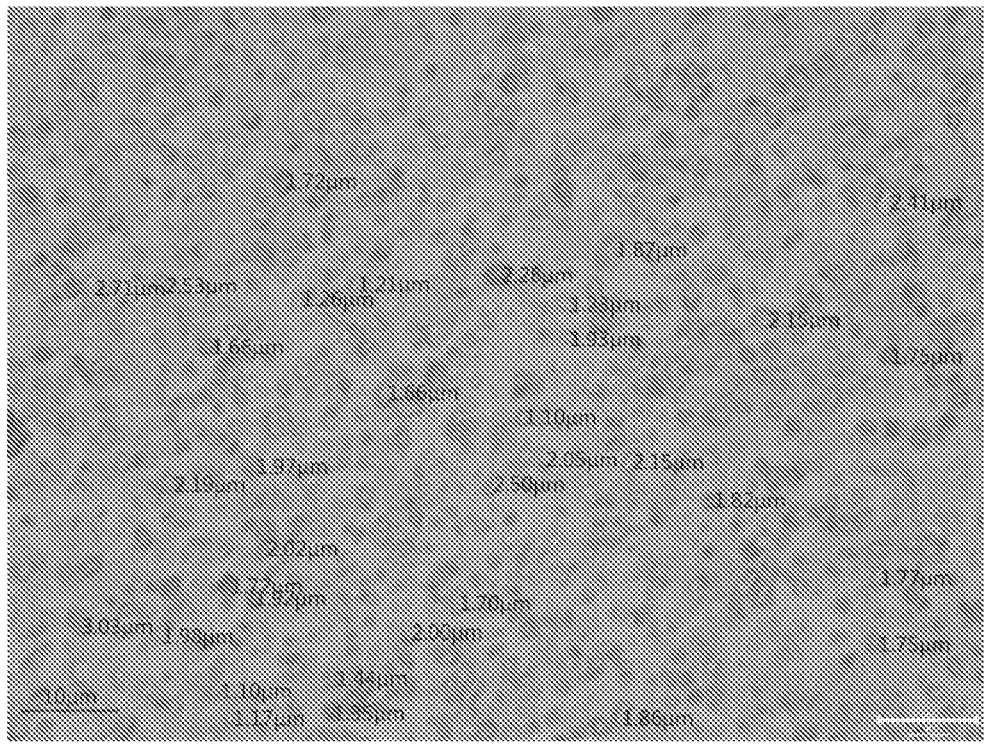
FIG. 11 shows a polarized light photomicrograph of the fulvestrant solid particles in the suspension after grinding in Example 3 after being placed at 60° C. for 20 days, on a 10 μm scale.
Figure 12:
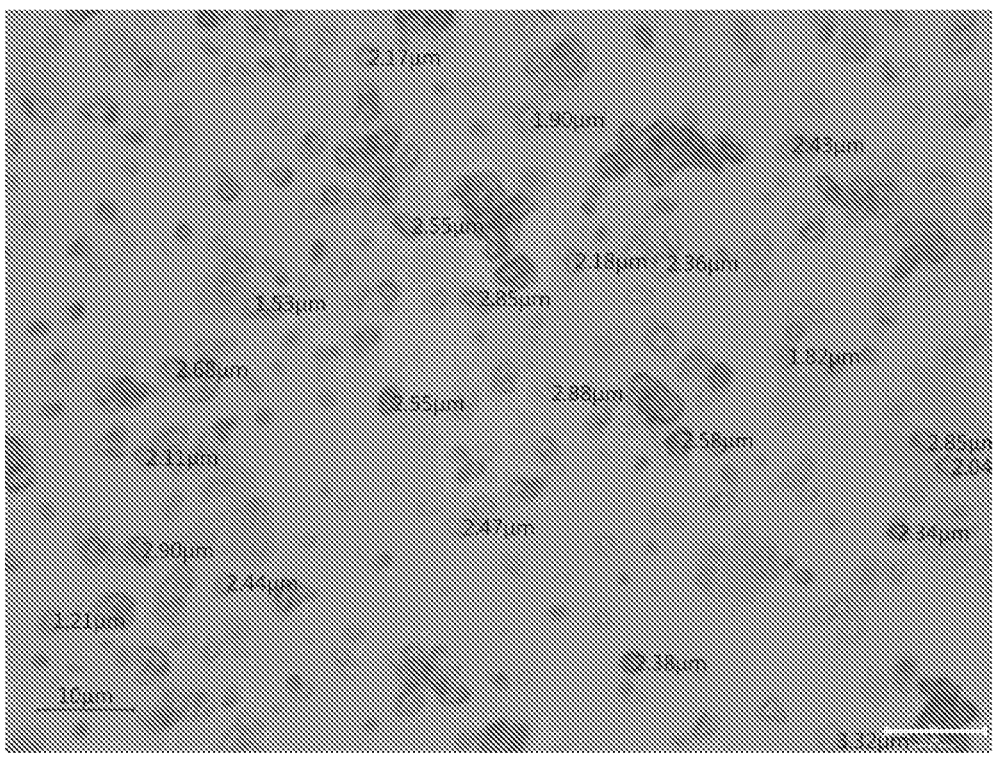
FIG. 12 shows a polarized light photomicrograph of the fulvestrant solid particles in the suspension after grinding in Example 3 after being placed at 40° C. for 20 days, on a 10 μm scale.
Figure 13:
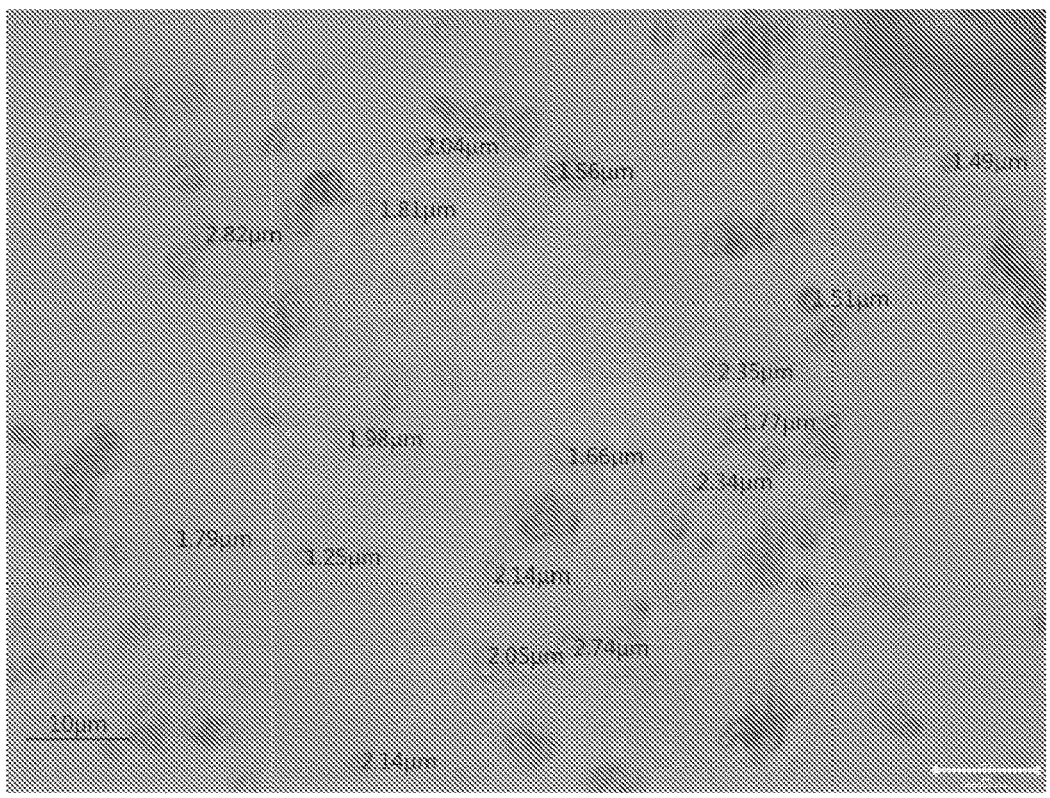
FIG. 13 shows a polarized light photomicrograph of the fulvestrant solid particles in the suspension after grinding in Example 3 after being placed at 40° C. for 30 days, on a 10 μm scale.
Figure 14:
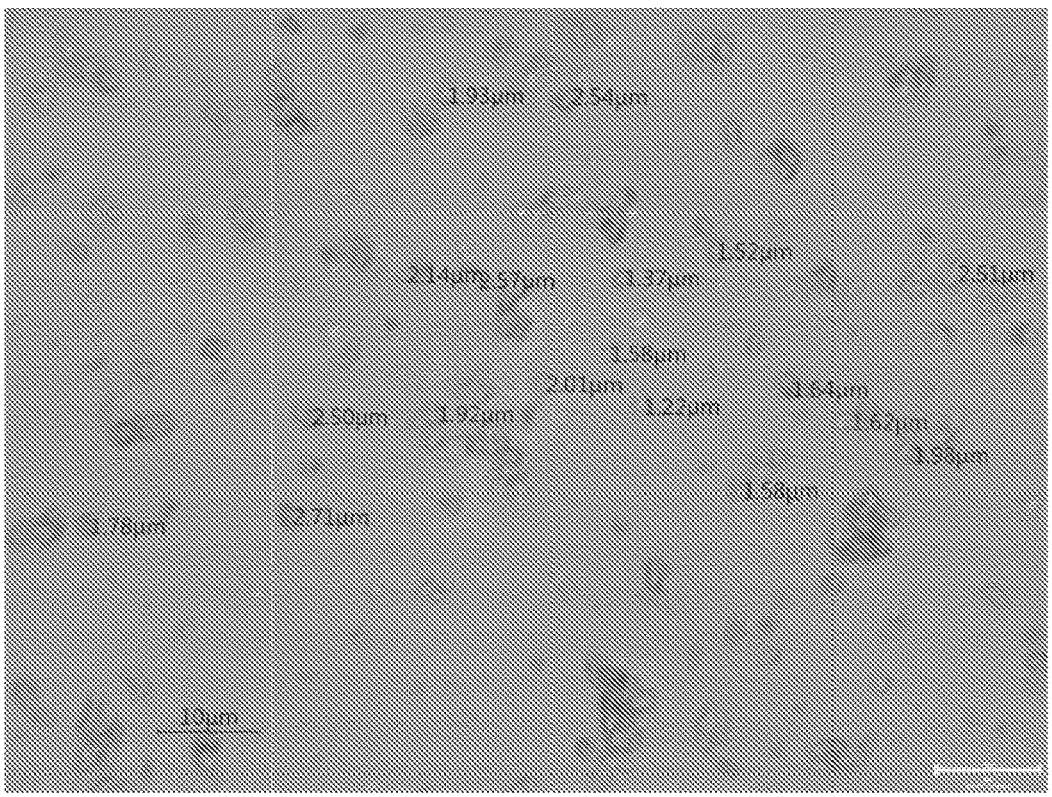
FIG. 14 shows a polarized light photomicrograph of the fulvestrant solid particles in the suspension after grinding in Example 3 after being placed at 25° C. for 30 days, on a 10 μm scale.
Figure 15:
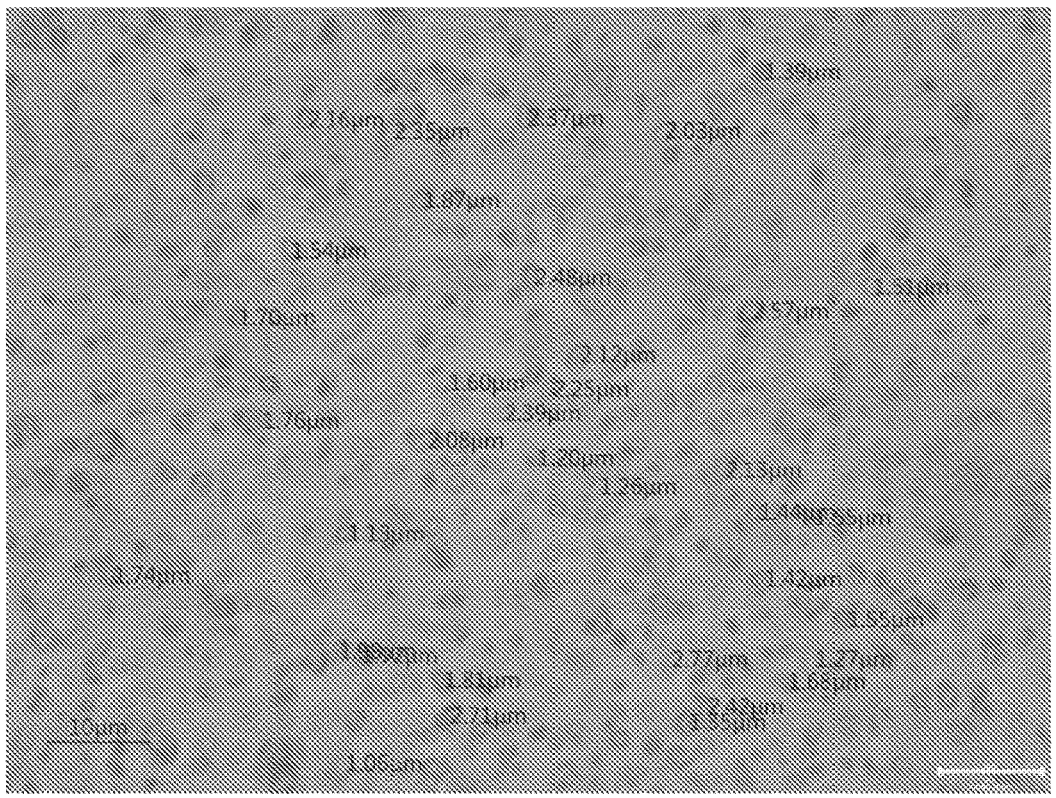
FIG. 15 shows a polarized light photomicrograph of the fulvestrant solid particles in the suspension after grinding in Example 3 after being placed at 4° C. for 30 days, on a 10 μm scale.

The fulvestrant suspension prepared in Example 3 was placed at −20° C., 4° C., 25° C., 40° C. or 60° C., and tested for related substances, the morphology, particle size distribution and crystalline form changes of the fulvestrant solid particles. The results are shown in Tables 8 and 9. The XRPD test patterns are shown in FIGS. 9 and 10. The particle size morphology of the fulvestrant solid particles is shown in FIGS. 11-15. The test for the related substances was performed according to the EP10.0 method.

TABLE 8

Related substances in the fulvestrant suspension prepared in Example 3 after being placed at different temperatures

| Placement conditions | Peak area (%, RRT) | | | | | |
|---|---|---|---|---|---|---|
| | Main peak | RRT 0.93 | RRT 1.21 | RRT 1.28 | RRT 1.48 | Total impurities |
| 4° C., 30 days | 99.73 | 0.06 | 0.05 | 0.02 | 0.03 | 0.27 |
| −20° C., 30 days | 99.73 | 0.06 | 0.05 | 0.02 | 0.04 | 0.28 |
| 25° C., 30 days | 99.73 | 0.06 | 0.05 | 0.02 | 0.04 | 0.29 |
| 40° C., 20 days | 99.70 | 0.06 | 0.05 | 0.02 | 0.04 | 0.30 |
| 40° C., 30 days | 99.73 | 0.06 | 0.05 | 0.02 | 0.01 | 0.26 |
| 60° C., 20 days | 99.65 | 0.07 | 0.05 | 0.03 | 0.03 | 0.36 |

TABLE 9

Particle size distribution in the fulvestrant suspension prepared in Example 3 after being placed at different temperatures

| Placement conditions | D10 (μm) | 1025 (μm) | D50 (μm) | D75 (μm) | D90 (μm) |
|---|---|---|---|---|---|
| 60° C., 20 days | 0.904 | 1.082 | 1.28 | 1.525 | 1.737 |
| 40° C., 30 days | 1.738 | 2.373 | 3.215 | 4.116 | 5.048 |
| 25° C., 30 days | 2.206 | 2.769 | 3.473 | 4.229 | 5.073 |
| 4° C., 30 days | 1.347 | 1.973 | 2.777 | 3.601 | 4.325 |
| 4° C., 40 days | 0.909 | 1.325 | 1.822 | 2.385 | 2.934 |

The test results of the related substances showed that the related substances in the suspension were slightly increased after grinding; after being placed under different conditions, the related substances in the suspension were not significantly increased. The maximum content of single impurities was 0.07% and the maximum content of total impurities was 0.36% under all conditions, so that the quality standards were met.

It can be seen from the particle size morphology (PLM) of FIGS. 11-15 that the morphology of fulvestrant solid particles in the samples remained unchanged under all conditions, and no significant increase in the particle size was found except for the aggregation of a small amount particles in some of the samples. Laser particle size analysis showed that the particle size of the fulvestrant solid particles in the suspensions did not exceed 5 μm under all conditions, was slightly increased at 25° C. and 40° C. (possibly related to the aggregation of the sample particles, but single particles remained unchanged), and was slightly reduced at 60° C.

The XRPD results of FIGS. 9 and 10 showed that the crystalline forms of the fulvestrant solid particles in the suspensions under different conditions were consistent with the initial fulvestrant solid particles, suggesting that there is no change in the crystalline form of the fulvestrant solid particles.

Example 4

TABLE 10

Formula of the suspension injection of Example 4

| Component | Ratio (%, W/W) | Feeding amount (g) |
|---|---|---|
| Fulvestrant | 25.00 | 5.00 |
| Tween 20 | 1.62 | 0.333 |
| Sodium carboxymethylcellulose | 1.00 | 0.20 |
| Mannitol | 2.89 | 14.467 |
| Anhydrous sodium dihydrogen phosphate | 0.43 | |
| Sodium hydroxide | q.s. to pH 7.4 | |
| Sterile water for injection | q.s. to 100 | |

According to the formula as shown in Table 10, 0.333 g of tween 20 was weighed, and 5.00 g of fulvestrant solid particles were added, followed by the addition of 4% mannitol-pH 7.4 anhydrous sodium dihydrogen phosphate solu-

TABLE 7

Related substances in the fulvestrant suspension prepared in Examples 1 and 2 after being placed at 4 °C

| | | Peak area (%), placed at 4° C. | | | | | | | | | | | | | | | |
|---|---|---|---|---|---|---|---|---|---|---|---|---|---|---|---|---|---|
| No. | Main peak | RRT 0.25 | RRT 0.36 | RRT 0.39 | RRT 0.43 | RRT 0.51 | RRT 0.88 | RRT 1.15 | RRT 1.19 | RRT 1.39 | RRT 1.49 | RRT 1.63 | RRT 1.88 | RRT 2.49 | RRT 2.85 | RRT 2.92 | Total impurities |
| Fulvestrant solid particle starting material | 99.84 | / | / | / | / | 0.01 | 0.05 | / | 0.04 | / | / | / | / | / | / | 0.03 | 0.05 |
| Fulvestrant suspension prepared in Example 1 14 days | 99.78 | / | / | / | 0.02 | 0.01 | 0.05 | / | 0.03 | / | 0.02 | 0.03 | / | / | / | 0.02 | 0.13 |
| Fulvestrant suspension prepared in Example 2 10 days | 99.59 | 0.01 | / | / | 0.16 | / | 0.05 | / | 0.03 | / | 0.03 | 0.03 | / | / | / | 0.02 | 0.3 | tion to make up to 19.80 g (the percentage here refers to the percentage of the mass of mannitol to the total volume of mannitol-pH 7.4 anhydrous sodium dihydrogen phosphate solution), and the mixture was stirred and mixed well to obtain a premixed solution.

The premixed solution and 97.5 g of 0.3 mm zirconium beads were added into a grinding jar (the volume ratio of the premixed solution to the zirconium beads is 2:3) for grinding for 27 h to obtain the fulvestrant pharmaceutical composition as a suspension injection. The grinding was performed in a ball mill, and the parameters of the planetary ball mill were set as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min.

Figure 16:
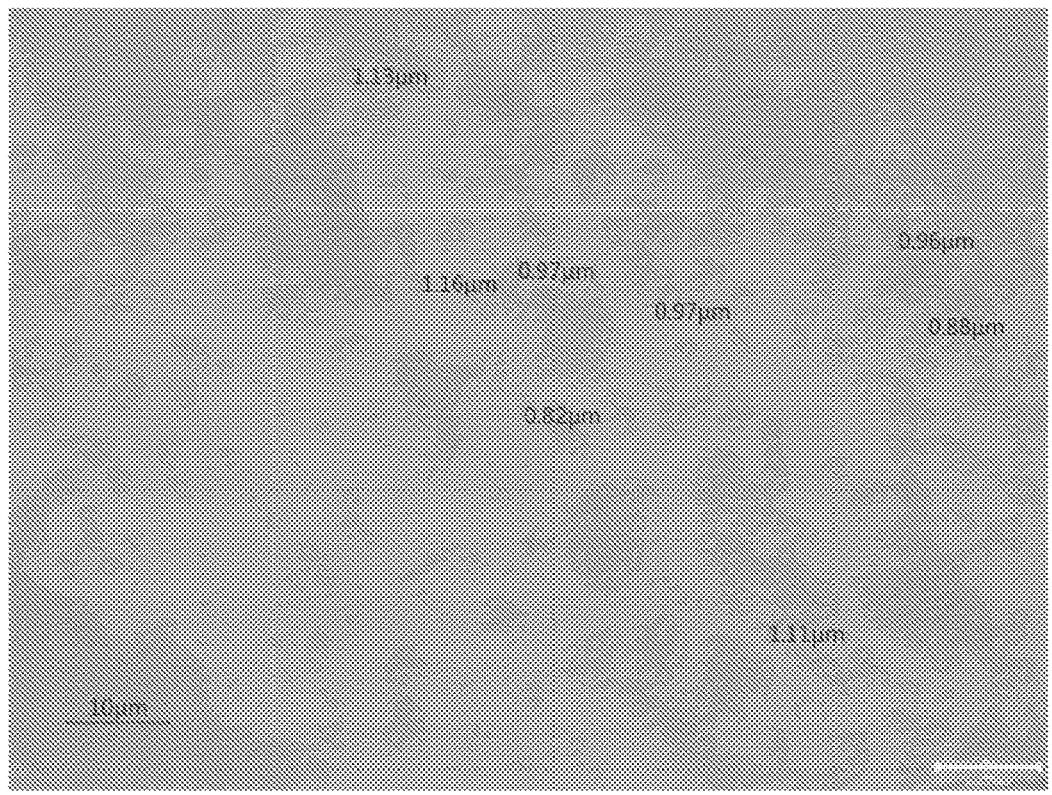
FIG. 16 shows a polarized light photomicrograph of the fulvestrant solid particles in the suspension after grinding in Example 4, on a 10 μm scale.

After the determination using a laser particle analyzer (the parameters were set as follows: the dispersion medium: water, the refractive index of the dispersion medium: 1.333, the absorbance of the sample material: 0.01, and the refractive index of the sample material: 1.521), the particle size distribution of the fulvestrant solid particles in the suspension after grinding for different periods of time is shown in Table 11. The particle size morphology of the fulvestrant solid particles in the suspension after grinding is shown in FIG. 16.

TABLE 11

Particle size distribution of fulvestrant in the suspension of Example 4

| Grinding time | D10 (μm) | D25 (μm) | D50 (μm) | D75 (μm) | D90 (μm) |
|---|---|---|---|---|---|
| 2 min | 1.799 | 2.362 | 3.29 | 4.341 | 5.353 |
| 5 min | 1.737 | 2.236 | 2.967 | 3.781 | 4.524 |
| 10 min | 1.597 | 2.058 | 2.699 | 3.397 | 4.116 |
| 30 min | 1.452 | 1.889 | 2.477 | 3.137 | 3.806 |
| 1 hr | 1.351 | 1.772 | 2.355 | 3.025 | 3.682 |
| 1.5 hrs | 1.211 | 1.629 | 2.153 | 2.73 | 3.3 |
| 3 hrs | 0.854 | 1.075 | 1.346 | 1.639 | 1.967 |
| 6 hrs | 0.914 | 1.094 | 1.304 | 1.551 | 1.795 |
| 9 hrs | 0.871 | 0.985 | 1.145 | 1.301 | 1.503 |
| 12 hrs | 0.894 | 1.026 | 1.171 | 1.328 | 1.534 |
| 27 hrs | 0.91 | 1.056 | 1.202 | 1.397 | 1.587 |

Example 5

TABLE 12

Formula of the suspension injection of Example 5

| Component | Ratio (%, W/W) | Feeding amount (g) |
|---|---|---|
| Fulvestrant | 25 | 5.00 |
| Tween 20 | 1.62 | 0.324 |
| Sodium carboxymethylcellulose | 1.00 | 0.20 |
| Mannitol | 2.89 | 14.476 |
| Anhydrous sodium dihydrogen phosphate | 0.43 | |
| Sodium hydroxide | q.s. to pH 7.4 | |
| Sterile water for injection | q.s. to 100 | |

According to the formula as shown in Table 12, 0.324 g of tween 20 was weighed, and 5.00 g of fulvestrant solid particles were added, followed by the addition of 4% mannitol-pH 7.4 anhydrous sodium dihydrogen phosphate solution to make up to 19.80 g (the percentage here refers to the percentage of the mass of mannitol to the total volume of mannitol-pH 7.4 anhydrous sodium dihydrogen phosphate solution), and the mixture was stirred and mixed well to obtain a premixed solution.

The premixed solution and 111.6 g of 0.6 mm zirconium beads were added into a grinding jar (the volume ratio of the premixed solution to the zirconium beads is 2:3) for grinding for 27 h to obtain the fulvestrant pharmaceutical composition as a suspension injection. The grinding was performed in a ball mill, and the parameters of the planetary ball mill were set as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min.

Figure 17:
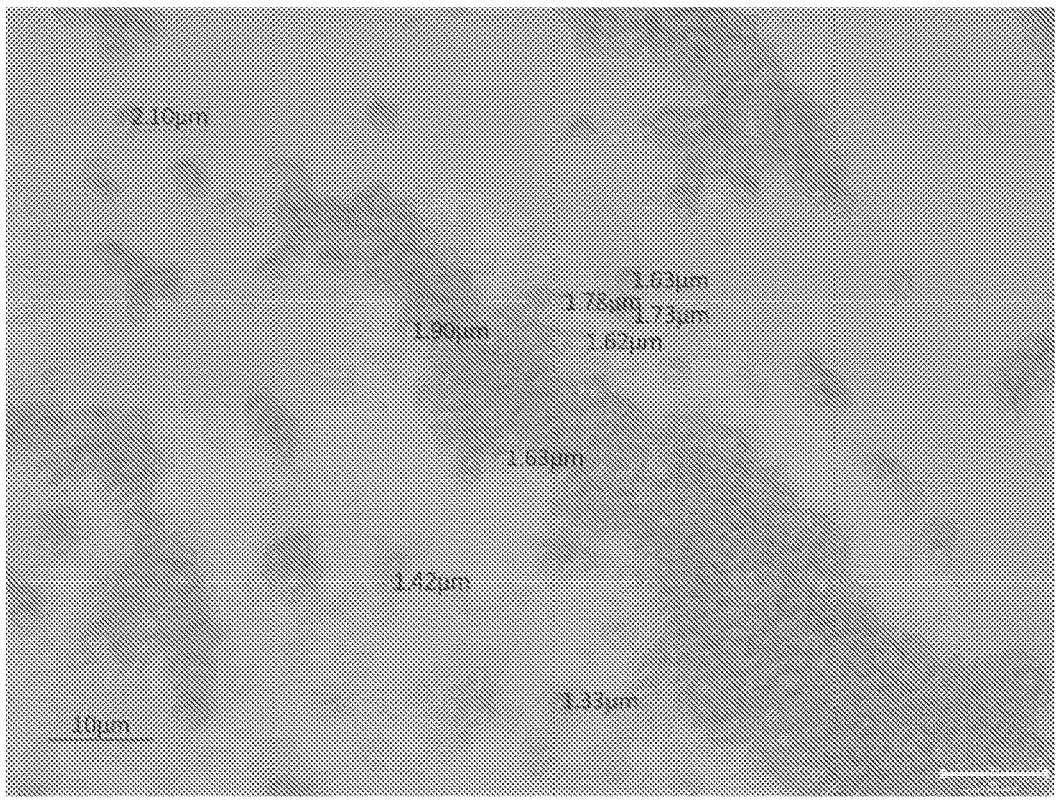
FIG. 17 shows a polarized light photomicrograph of the fulvestrant solid particles in the suspension after grinding in Example 5, on a 10 μm scale.

After the determination using a laser particle analyzer (the parameters were set as follows: the dispersion medium: water, the refractive index of the dispersion medium: 1.333, the absorbance of the sample material: 0.01, and the refractive index of the sample material: 1.521), the particle size distribution of the fulvestrant solid particles in the suspension after grinding for different periods of time is shown in Table 13, The particle size morphology of the fulvestrant solid particles in the suspension after grinding is shown in FIG. 17.

TABLE 13

Particle size distribution of fulvestrant in the suspension of Example 5

| Grinding time | D10 (μm) | D25 (μm) | D50 (μm) | D75 (μm) | D90 (μm) |
|---|---|---|---|---|---|
| 3 hrs | 0.882 | 1.075 | 1.307 | 1.581 | 1.881 |
| 6 hrs | 0.841 | 0.98 | 1.207 | 1.509 | 1.841 |
| 9 hrs | 0.886 | 1.074 | 1.29 | 1.551 | 1.816 |
| 12 hrs | 0.915 | 1.093 | 1.307 | 1.561 | 1.825 |
| 27 hrs | 0.92 | 1.075 | 1.241 | 1.469 | 1.644 |

Example 6

TABLE 14

Formula of the suspension injection of Example 6

| Component | Ratio (%, W/W) | Feeding amount (g) |
|---|---|---|
| Fulvestrant | 25 | 5.00 |
| Tween 20 | 1.62 | 0.328 |
| Sodium carboxymethylcellulose | 1.00 | 0.20 |
| Mannitol | 2.89 | 14.472 |
| Anhydrous sodium dihydrogen phosphate | 0.43 | |
| Sodium hydroxide | q.s. to pH 7.4 | |
| Sterile water for injection | q.s. to 100 | |

According to the formula as shown in Table 14, 0.328 g of tween 20 was weighed, and 5.0 g of fulvestrant solid particles were added, followed by the addition of 4% mannitol-pH 7.4 anhydrous sodium dihydrogen phosphate solution to make up to 19.80 g (the percentage here refers to the percentage of the mass of mannitol to the total volume of mannitol-pH 7.4 anhydrous sodium dihydrogen phosphate solution), and the mixture was stirred and mixed well to obtain a premixed solution.

The premixed solution and 112.0 g of 1.0 mm zirconium beads were added into a grinding jar (the volume ratio of the premixed solution to the zirconium beads is 2:3) for grinding for 27 h to obtain the fulvestrant pharmaceutical composition as a suspension injection. The grinding was performed in a ball mill, and the parameters of the planetary ball mill were set as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min.

Figure 18:
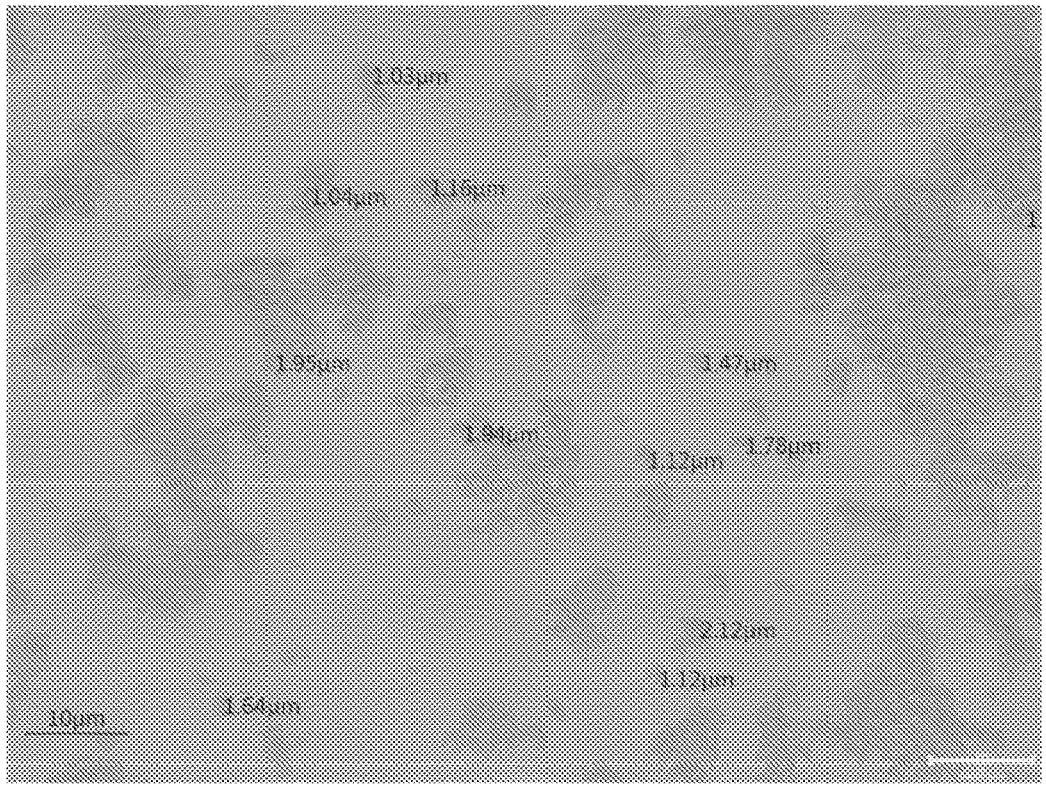
FIG. 18 shows a polarized light photomicrograph of the fulvestrant solid particles in the suspension after grinding in Example 6, on a 10 μm scale.

After the determination using a laser particle analyzer (the parameters were set as follows: the dispersion medium: water, the refractive index of the dispersion medium: 1.333, the absorbance of the sample material: 0.01, and the refractive index of the sample material: 1.521), an appropriate amount of the suspension was weighed, and tested for the fulvestrant content and related substances according to the EP10.0 method. The particle size distribution of the fulvestrant solid particles in the suspensions after grinding for different periods of time is shown in Table 15. The particle size morphology of the fulvestrant solid particles in the suspension after grinding is shown in FIG. 18.

TABLE 15

Particle size distribution of fulvestrant in the suspension of Example 6

| Grinding time | D10 (μm) | D25 (μm) | D50 (μm) | D75 (μm) | D90 (μm) |
|---|---|---|---|---|---|
| 3 hrs | 0.838 | 1.041 | 1.388 | 1.87 | 2.376 |
| 6 hrs | 0.852 | 1.059 | 1.416 | 1.904 | 2.406 |
| 9 hrs | 0.906 | 1.087 | 1.327 | 1.629 | 1.969 |
| 12 hrs | 0.976 | 1.168 | 1.43 | 1.708 | 2.007 |
| 27 hrs | 1.058 | 1.235 | 1.493 | 1.795 | 2.058 |

Example 7

TABLE 16

Formula of the suspension injection of Example 7

| Component | Ratio (%, w/w) |
|---|---|
| Fulvestrant | 25.00 |
| Tween 20 | 1.62 |
| Sodium carboxymethylcellulose | 0.20 |
| Mannitol | 2.29 |
| Anhydrous sodium dihydrogen phosphate | 0.09 |
| Anhydrous disodium hydrogen phosphate | 0.42 |
| Sterile water for injection | q.s. 100 (70.38) |

According to the formula as shown in Table 16, the raw and auxiliary materials were weighed and mixed well, followed by the addition of 1.5-fold volume of 0.6 mm zirconium beads, and the mixture was placed in a grinding jar for grinding for 3 h to obtain the fulvestrant pharmaceutical composition, which was recorded as batch 1. The grinding was performed in a ball mill, and the parameters of the planetary ball mill were set as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min.

Figure 19:
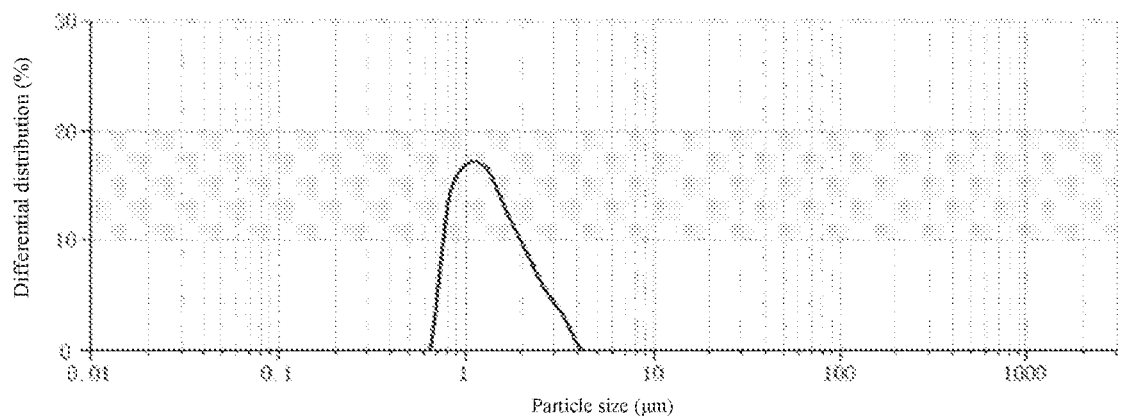
FIG. 19 shows particle size distribution of the fulvestrant solid particles in the suspension after grinding in Example 7.
Figure 20:
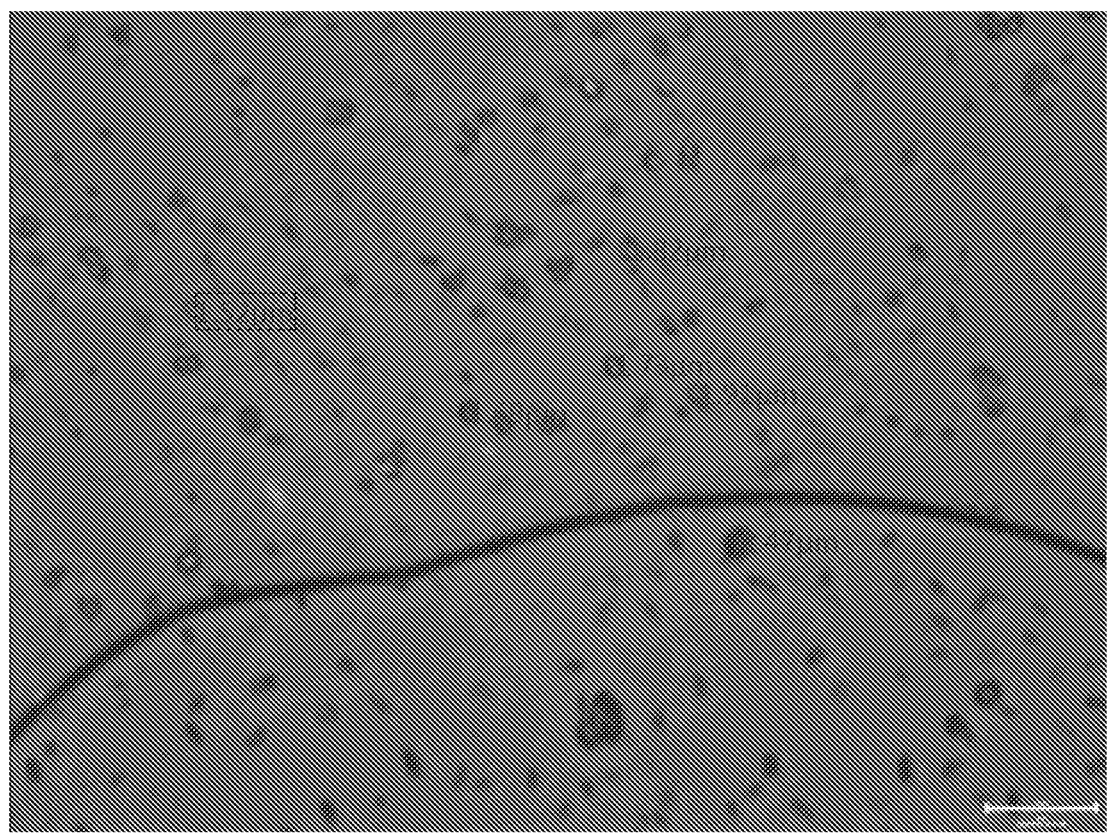
FIG. 20 shows a particle size morphology of the fulvestrant solid particles in the suspension after grinding in Example 7, on a 10 μm scale.

After the determination using a laser particle analyzer (the parameters were set as follows: the dispersion medium: water, the refractive index of the dispersion medium: 1.333, the absorbance of the sample material: 0.01, and the refractive index of the sample material: 1.521), an appropriate amount of the suspension was weighed, and tested for the fulvestrant content and related substances according to the EP10.0 method. The content and particle size distribution of the fulvestrant solid particles in the suspension after grinding are shown in Table 17. The particle size distribution of the fulvestrant solid particles in the suspension after grinding is shown in FIG. 19 and the morphology of the fulvestrant solid particles in the suspension after grinding is shown in FIG. 20. The related substances are shown in Table 19.

Example 8

TABLE 18

Formula of the suspension injection of Example 8

| Component | Ratio (%, w/w) |
|---|---|
| Fulvestrant | 25.00 |
| Tween 20 | 1.62 |
| Sodium carboxymethylcellulose | 0.20 |
| Mannitol | 2.29 |
| Anhydrous sodium dihydrogen phosphate | 0.09 |
| Anhydrous disodium hydrogen phosphate | 0.42 |
| Sterile water for injection | q.s. 100 (70.38) |

According to the formula as shown in Table 18, the raw and auxiliary materials were weighed and mixed well, followed by the addition of 3-fold volume of 1 mm zirconium beads, and the mixture was placed in a grinding jar for grinding for 5 min to obtain the fulvestrant pharmaceutical composition, which was recorded as batch 2. The grinding was performed in a ball mill, and the parameters of the planetary ball mill were set as follows: fixed parameters: the diameter of the revolution plate: about 191 mm, the diameter of the rotation cup: about 71 mm, the height of the rotation cup: about 70 mm, the capacity of the rotation cup: 100 mL, the revolution speed of the revolution plate: 10 r/min, and the rotation speed: 720 r/min.

Figure 21:
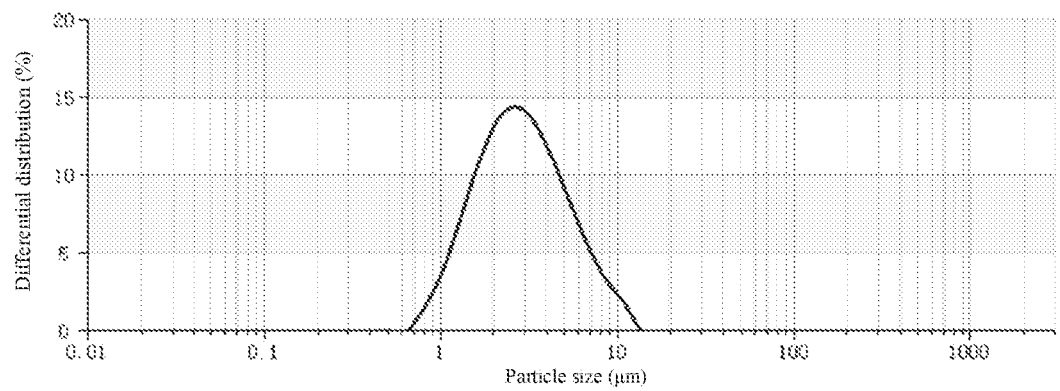
FIG. 21 shows particle size distribution of the fulvestrant solid particles in the suspension after grinding in Example 8.
Figure 22:
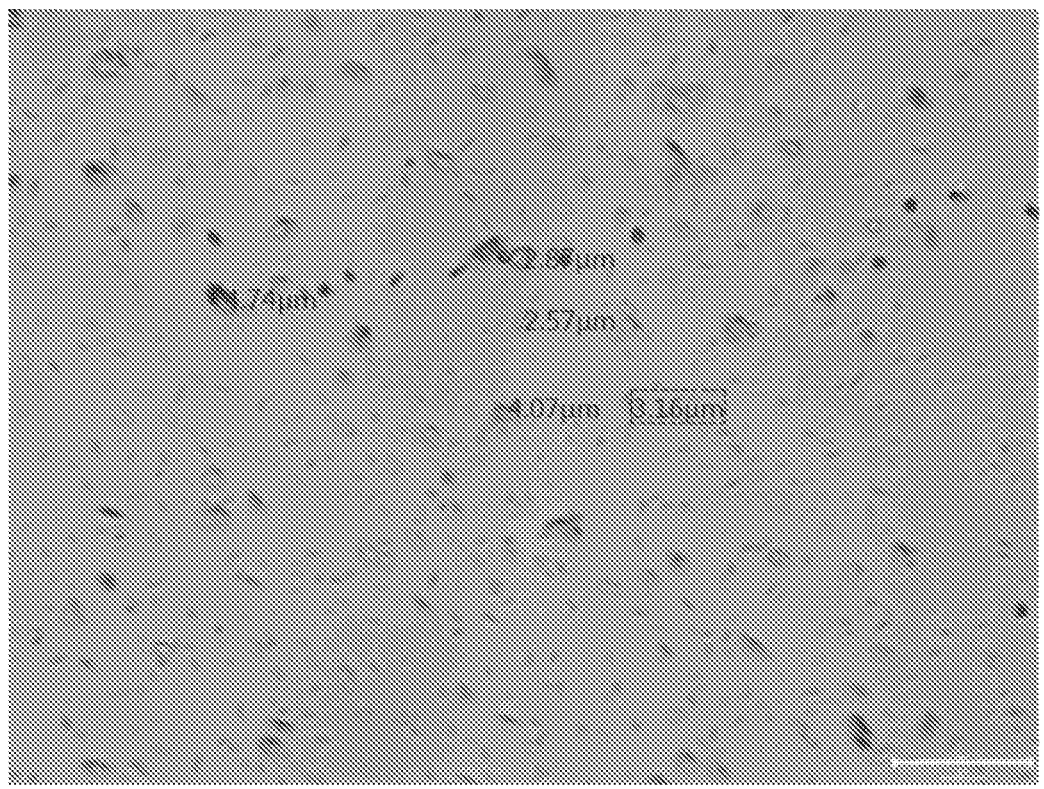
FIG. 22 shows a particle size morphology of the fulvestrant solid particles in the suspension after grinding in Example 8, on a 10 μm scale.

After the determination using a laser particle analyzer (the parameters were set as follows: the dispersion medium: water, the refractive index of the dispersion medium: 1.333, the absorbance of the sample material: 0.01, and the refractive index of the sample material: 1.521), an appropriate amount of the suspension was weighed, and tested for the fulvestrant content and related substances according to the EP10.0 method. The content and particle size distribution of the fulvestrant solid particles in the suspension after grinding are shown in Table 17. The particle size distribution of the fulvestrant solid particles in the suspension after grinding is shown in FIG. 21 and the morphology of the fulvestrant solid particles in the suspension after grinding is shown in FIG. 22. The related substances are shown in Table 19.

Example 9

TABLE 20

Formula of the suspension injection of Example 9

| Component | Ratio (%, w/w) |
|---|---|
| Fulvestrant | 25 |
| Tween 20 | 1.62 |
| Sodium carboxymethylcellulose | 0.2 |
| Mannitol | 2.29 |
| Anhydrous sodium dihydrogen phosphate | 0.09 |
| Anhydrous disodium hydrogen phosphate | 0.42 |
| Sterile water for injection | q.s. 100 (70.38) |

According to the formula as shown in Table 20, the raw and auxiliary materials were weighed and mixed well to obtain the fulvestrant pharmaceutical suspension, which was recorded as batch 3. The API was obtained by jet milling.

Figure 23:
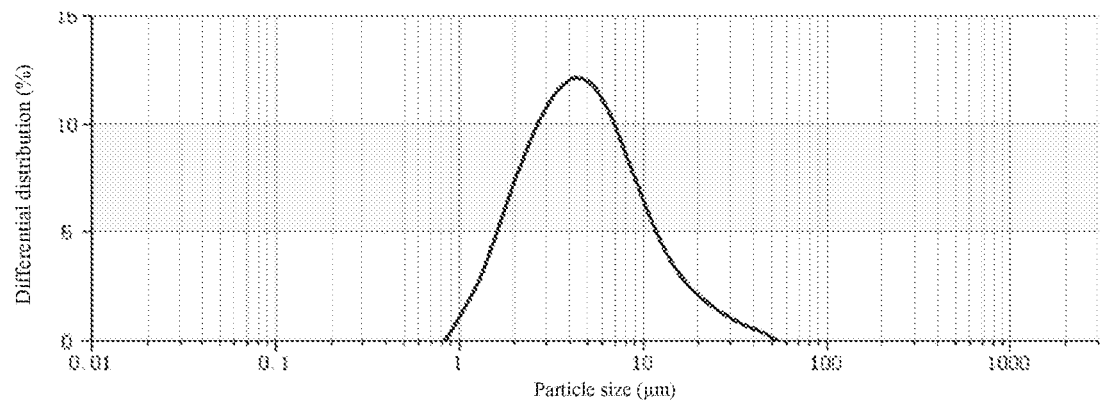
FIG. 23 shows particle size distribution of the fulvestrant solid particles in the suspension after grinding in Example 9.
Figure 24:
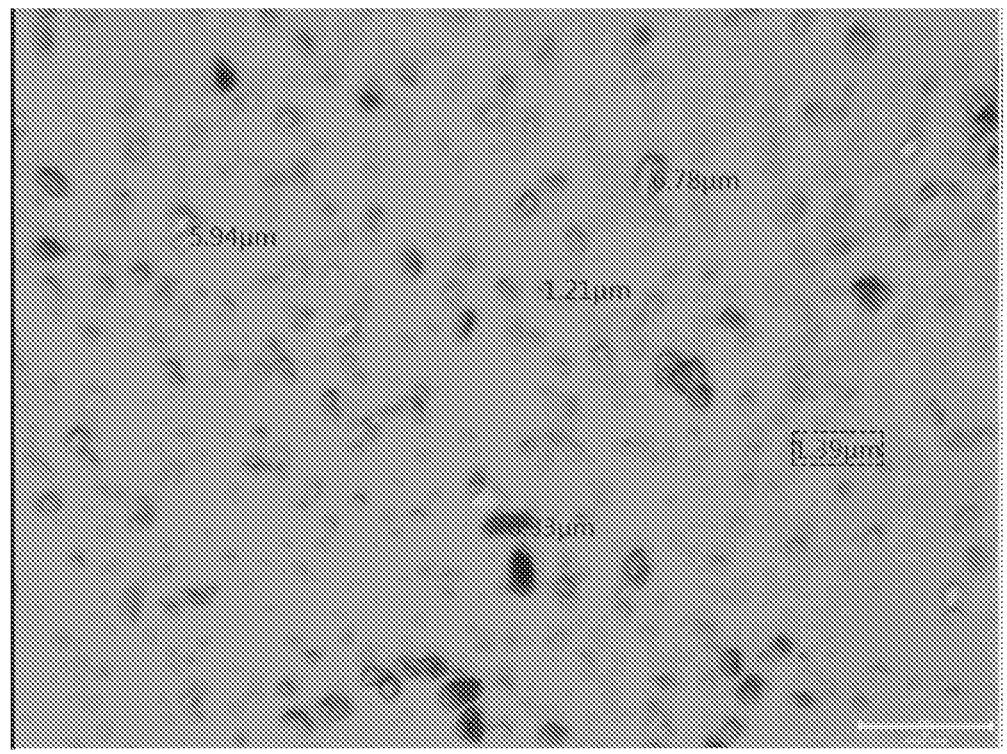
FIG. 24 shows a particle size morphology of the fulvestrant solid particles in the suspension after grinding in Example 9, on a 10 μm scale.
Figure 25:
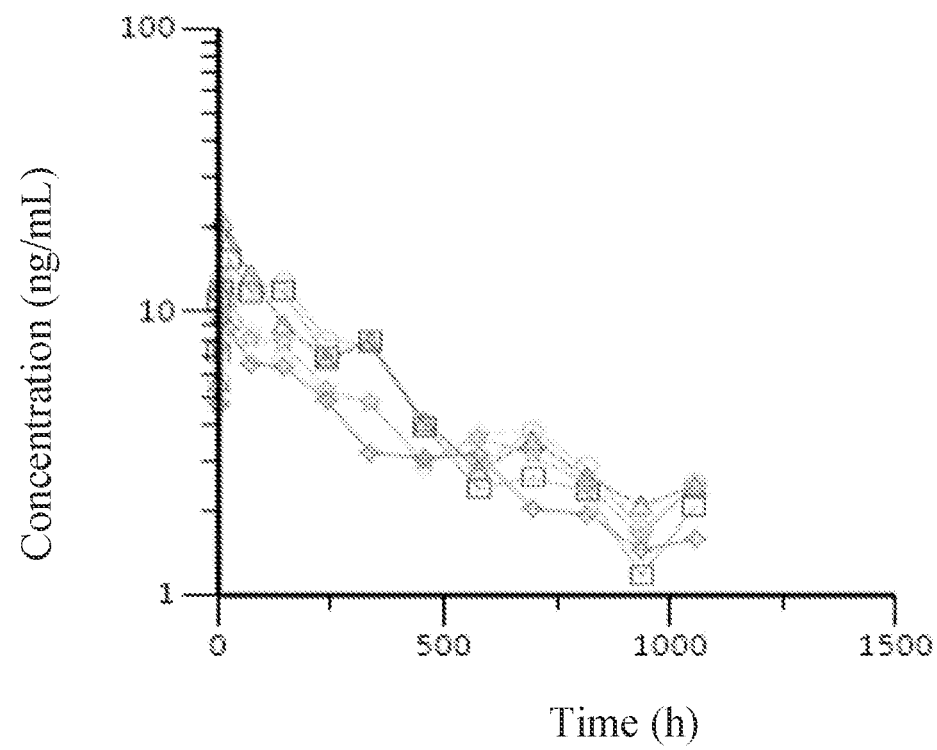
FIG. 25 shows pharmacokinetic profiles of fulvestrant in formulation No. 1 of Example 11 (i.e., marketed comparative fulvestrant formulation); wherein
— represents the pharmacokinetic profile in animal 1;
— represents the pharmacokinetic profile in animal 2;
— represents the pharmacokinetic profile in animal 3;
— represents the pharmacokinetic profile in animal 4;
— represents the pharmacokinetic profile in animal 5; and
— represents the pharmacokinetic profile in animal 6.
Figure 26:
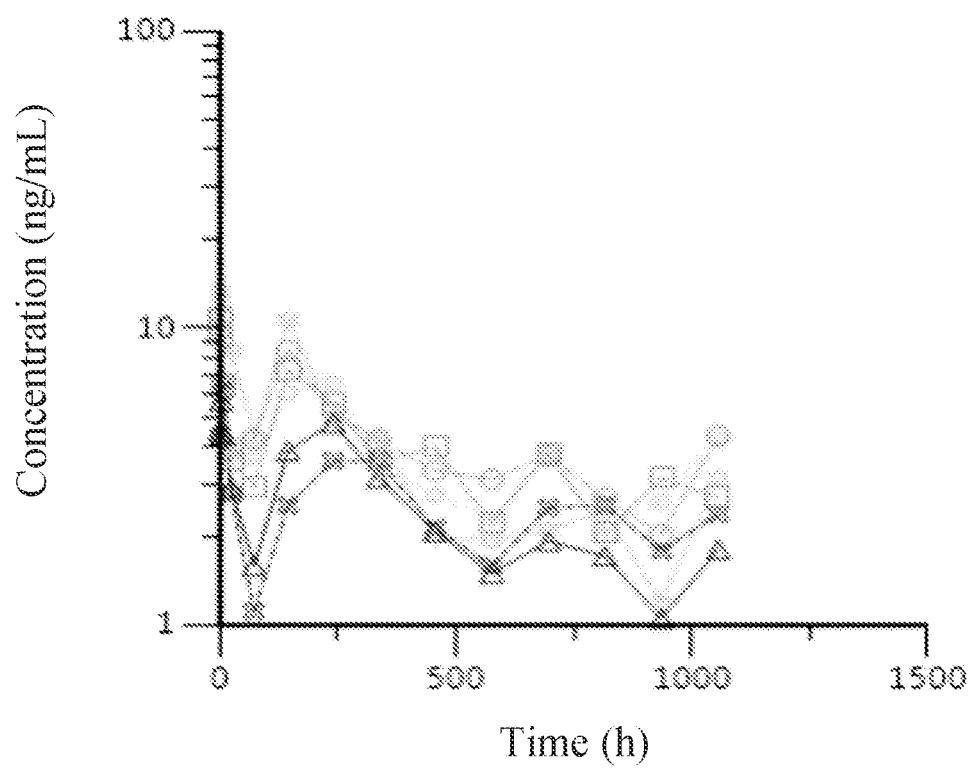
FIG. 26 shows pharmacokinetic profiles of fulvestrant in formulation No. 2 of Example 11; wherein
— represents the pharmacokinetic profile in animal 1;
— represents the pharmacokinetic profile in animal 2;
— represents the pharmacokinetic profile in animal 3;
— represents the pharmacokinetic profile in animal 4;
— represents the pharmacokinetic profile in animal 5; and
— represents the pharmacokinetic profile in animal 6.
Figure 27:
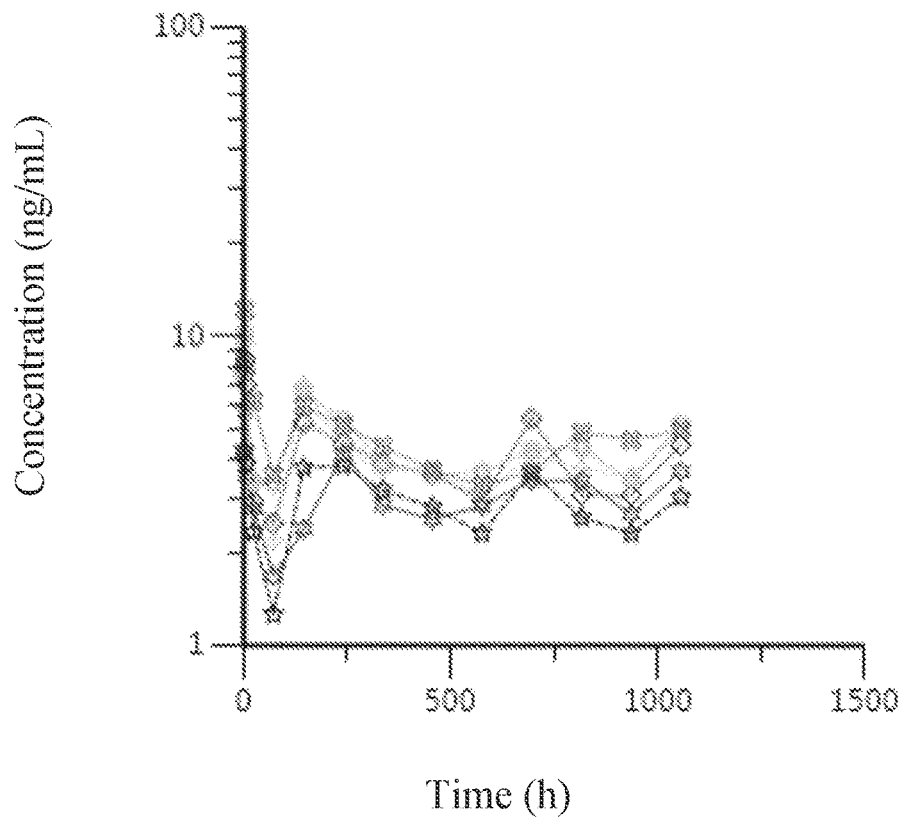

After the determination using a laser particle analyzer (the parameters were set as follows: the dispersion medium: water, the refractive index of the dispersion medium: 1.333, the absorbance of the sample material: 0.01, and the refractive index of the sample material: 1.521), an appropriate amount of the suspension was weighed, and tested for the fulvestrant content and related substances according to the EP10.0 method. The content and particle size distribution of the fulvestrant solid particles in the suspension are shown in Table 17. The particle size distribution of the fulvestrant solid particles in the suspension after grinding is shown in FIG. 23 and the morphology of the fulvestrant solid particles in the suspension after grinding is shown in FIG. 24. The related substances are shown in Table 19.

TABLE 17

API concentration, particle size and particle size distribution in the fulvestrant suspensions of Examples 7-9

| Batch | Concentration (mg/mL) | Particle size (μm) | | | | |
|---|---|---|---|---|---|---|
| | | Dv(10) | Dv(25) | Dv(50) | Dv(75) | Dv(90) |
| 1 | 341.9 | 0.806 | 0.922 | 1.127 | 1.459 | 1.955 |
| 2 | 263.8 | 1.373 | 1.840 | 2.610 | 3.781 | 5.191 |
| 3 | 270.1 | 1.856 | 2.675 | 4.215 | 6.570 | 9.982 |

Example 10

The formulations obtained in Examples 7, 8 and 9 (recorded as formulation Nos. 2, 3 and 4, respectively) and the marketed comparative formulation fulvestrant injection FASLODEX (5 mL: 250 mg, VETTER Pharma-fertigung GmbH & Co KG, Germany, lot No. RD693, expiration date: August, 2023, recorded as formulation No. 1) were used. The formulation Nos. 2, 3 and No. 1 were placed for the stability under long-term conditions (25±2° C., 60%±5% RH) and accelerated conditions (40±2° C., 75%±5% RH) as shown in Table 21, and tested for related substances of fulvestrant according to the EP10.0 method. The results are shown in Table 19, Meanwhile, the particle size and particle size distribution of the formulation Nos. 2 and 3 were also determined. The results are shown in Tables 22 and 23.

The stability results showed that the levels of the degradation impurities 6-keto fulvestrant and fulvestrant sulphone, the unknown single impurities and the total impurities in the self-made fulvestrant suspension were all lower than those of the comparative formulation fulvestrant injection FASLODEX under the same conditions, suggesting that the stability of the self-made fulvestrant suspension is superior to that of the marketed comparative formulation.

TABLE 21

Placement for the stability of the formulation Nos. 2 and 3 formulations and the comparative formulation

| Sample | Long-term conditions (25 ± 2° C., 60% ± 5% RH) | Accelerated conditions (40 ± 2° C., 75% ± 5% RH) |
|---|---|---|
| Marketed comparative formulation | 1 month, 3 months | 10 days, 30 days |
| Formulation Nos. 2 and 3 | 1 month, 3 months | 1 month, 2 months, 3 months |

TABLE 22

Particle size and particle size distribution in the fulvestrant suspension of Example 7 (formulation No. 2)

| Placement conditions | Time | Particle size (μm) | | | | |
|---|---|---|---|---|---|---|
| | | Dv(10) | Dv(25) | Dv(50) | Dv(75) | Dv(90) |
| 25 ± 2° C., 60% ± 5% RH | Day 0 | 0.806 | 0.922 | 1.127 | 1.459 | 1.955 |
| | 1 month | 0.852 | 1.094 | 1.518 | 2.087 | 2.647 |
| | 3 months | 0.747 | 0.930 | 1.252 | 1.777 | 2.334 |
| 40 ± 2° C., 75% ± 5% RH | 1 month | 0.797 | 0.916 | 1.119 | 1.457 | 1.962 |
| | 2 months | 0.759 | 0.923 | 1.168 | 1.493 | 1.857 |
| | 3 months | 0.852 | 1.038 | 1.262 | 1.540 | 1.822 |

TABLE 23

Particle size and particle size distribution in the fulvestrant suspension of Example 8 (formulation No. 3)

| Placement conditions | Time | Particle size (μm) | | | | |
|---|---|---|---|---|---|---|
| | | Dv(10) | Dv(25) | Dv(50) | Dv(75) | Dv(90) |
| 25 ± 2° C., 60% ± 5% RH | Day 0 | 1.373 | 1.840 | 2.610 | 3.781 | 5.191 |
| | 1 month | 1.624 | 2.132 | 2.877 | 3.788 | 4.727 |
| | 3 months | 1.328 | 1.645 | 2.215 | 3.221 | 3.662 |
| 40 ± 2° C., 75% ± 5% RH | 1 month | 1.642 | 2.195 | 3.152 | 4.357 | 5.541 |
| | 2 months | 1.484 | 1.995 | 2.682 | 3.442 | 4.194 |

TABLE 19

Related substances for the stability of Example 7 (formulation No. 2) and Example 8 (formulation No. 3) and the comparative formulation

| Sample name | Placement conditions | Time | Single impurities (%) | | | | | | | | Total (%) impurities |
| --- | --- | --- | --- | --- | --- | --- | --- | --- | --- | --- | --- |
| | | | 6-keto fulvestrant* | 6,7-fulvestrant | Fulvestrant β-isomer | Fulvestrant sulphone* | Fulvestrant bromo analogue | Fulvestrant extended | Fulvestrant sterol dimer | Other maximum | |
| Example 7 Fulvestrant Suspension | Long-term | Day 0 | ND | ND | ND | ND | ND | ND | ND | 0.06 | 0.06 |
| | | 1 month | ND | ND | ND | 0.02 | ND | ND | ND | 0.06 | 0.06 |
| | | 3 months | ND | ND | ND | 0.04 | ND | ND | ND | 0.07 | 0.12 |
| | Accelerated | 1 month | ND | ND | ND | 0.03 | ND | ND | ND | 0.06 | 0.06 |
| | | 2 months | ND | ND | ND | 0.04 | ND | ND | ND | 0.07 | 0.12 |
| | | 3 months | 0.01 | ND | ND | 0.05 | ND | ND | ND | 0.07 | 0.17 |
| Example 8 Fulvestrant Suspension | Long-term | Day 0 | ND | ND | ND | ND | ND | ND | ND | 0.06 | 0.06 |
| | | 1 month | ND | ND | ND | 0.02 | ND | ND | ND | 0.06 | 0.06 |
| | | 3 months | ND | ND | ND | 0.04 | ND | ND | ND | 0.06 | 0.11 |
| | Accelerated | 1 month | ND | ND | ND | 0.03 | ND | ND | ND | 0.06 | 0.06 |
| | | 2 months | ND | ND | ND | 0.05 | ND | ND | ND | 0.08 | 0.18 |
| | | 3 months | 0.01 | ND | ND | 0.06 | ND | ND | ND | 0.08 | 0.19 |
| FASLODEX (LOT: RD693) | Long-term | Day 0 | 0.02 | ND | ND | 0.16 | ND | ND | ND | 0.07 | 0.37 |
| | | 1 month | 0.02 | ND | ND | 0.17 | ND | ND | ND | 0.09 | 0.46 |
| | | 3 months | 0.02 | ND | ND | 0.19 | ND | ND | ND | 0.09 | 0.52 |
| | Accelerated | 10 days | 0.02 | ND | ND | 0.22 | ND | 0.04 | ND | 0.09 | 0.57 |
| | | 1 month | 0.02 | ND | ND | 0.16 | ND | ND | ND | 0.09 | 0.45 |

Note:
ND means not detected;
*denotes the degradation product of fulvestrant;
6-keto fulvestrant, 6,7-fulvestrant, fulvestrant β-isomer, fulvestrant sulphone, fulvestrant bromine analogue, fulvestrant extended, and fulvestrant sterol dimer.

Example 11

The formulations obtained in Examples 7, 8 and 9 (formulation Nos. 2, 3 and 4, respectively) were diluted to 50 mg/mL with a diluent. The diluent comprises the following components: 1.62% tween 20, 0.2% sodium carboxymethylcellulose, 2.29% mannitol, 0.09% anhydrous sodium dihydrogen phosphate, and 0.42% anhydrous disodium hydrogen phosphate. The diluted fulvestrant suspension and the marketed comparative formulation fulvestrant injection FASLODEX (i.e., the formulation No. 1, 50 mg/mL, VETTER, Pharma-fertigung GmbH & Co KG, Germany, lot No. RD693, expiration date: August, 2023) were intramuscularly injected at a fulvestrant dose of 15 mg/kg (0.3 mL/kg) into the lateral thigh of SPF-grade Wistar rats weighing 217-235 g and aged 6-9 weeks (Zhejiang Vital River Laboratory Animal Technology Co., Ltd., certificate No. 110011200105465684, license No. SYXK (Su) 2018-0034), 6 animals per group. Clinical observations were made after the administration, with 2 observations on the first day of administration (D1): before the administration and in the afternoon of the day after the administration, and 1 observation everyday thereafter for a total of 45 days. Clinical observations involve skin, hair, eyes, ears, nose, oral cavity, chest, abdomen, urogenital area, limbs and other sites, and comprise breath, movement, urination, defecation and behavioral changes as well as muscle irritation responses at the site of administration. In addition, blood samples were collected before the administration (0 h, D-1), and 1 h, 3 h, 7 h, 24 h, D4 (72 h), D7 (144 h), D11 (240 h), D15(336 h), D20 (456 h), D25 (576 h), D30 (696 h), D35 (816 h), D40 (936 h) and D45 (1056 h) after the D1 administration, bioanalysis was performed and pharmacokinetic parameters Tmax, Cmax, AUX (0-t), AUC (0-∞), T½, MRT, CL, Vz and the like of each group were calculated using a non-compartmental model of WinNolin version 8.1. On D45 after the administration, animals were dissected and the site of administration was histopathologically examined for inflammatory responses and drug residues.

No abnormalities were observed in clinical observations, body weight, irritation observation at the site of administration, and gross anatomy of the site of administration in all animal subjects in each dose group, no inflammation or drug residues were observed at the site of administration, and no abnormalities related to the administration of the test sample were observed in histopathological examination.

Pharmacokinetic parameters for 15 mg/kg fulvestrant formulation Nos. 1, 2, 3 and 4 (formulation No. 1 represents the marketed comparative fulvestrant formulation; formulation No. 2 represents the fulvestrant formulation prepared in Example 7, formulation No. 3 represents the fulvestrant formulation prepared in Example 8, and formulation No. 4 represents the fulvestrant formulation prepared in Example 9) intramuscularly injected into Wistar rats at a single dose are shown in Table 24. The pharmacokinetic profiles for 15 mg/kg fulvestrant formulation Nos. 1, 2, 3 and 4 intramuscularly injected into Wistar rats at a single dose are shown in FIGS. 25, 26, 27 and 28, respectively, and the mean pharmacokinetic profiles of the formulation Nos. 1, 2, 3 and 4 are shown in FIG. 29.

After 15 mg/kg formulation No. 1 (the marketed comparative fulvestrant formulation) was intramuscularly injected into Wistar rats at a single dose, the Cmax of fulvestrant in plasma was 13.5±4.32 ng/mL, the area under the drug concentration-time curve AUCINF_obs was 6350±949 h*ng/mL, AUClast was 5000±932 h*ng/mL, the drug's terminal elimination half-life T½_Z was 413±88.0 h, the clearance rate Cl_obs was 2410±433 mL/h/kg, the mean residence time MRTINF_obs was 641±136 h, and the distribution volume Vz_obs was 1,450,000±421,000 mL/kg.

After 15 mg/kg formulation No. 2 (the fulvestrant formulation prepared in Example 7) was intramuscularly injected into Wistar rats at a single dose, the Cmax of fulvestrant in plasma was 10.0±3.16 ng/mL, the area under the drug concentration-time curve AUCINF_obs was 6990±2010 h*ng/mL, AUClast was 3490±745 h*ng/mL, the drug's terminal elimination half-life T½_Z was 776±300 h, the clearance rate Cl_obs was 2340±814 mL/h/kg, the mean residence time MRTINF_obs was 1310±443 h, and the distribution volume Vz_obs was 2,470,000±881,000 mL/kg.

terminal elimination half-life T½_Z was 5300±9230 h, the clearance rate Cl_obs was 1550±1150 mL/h/kg, the mean residence time MRTINF_obs was 7820±13,300 h, and the distribution volume Vz_obs was 3,170,000±571,000 mL/kg.

The results showed that after 15 mg/kg formulation was intramuscularly injected into Wistar rats at a single dose, the Cmax was ranked in descending order as the formulation No. 1>the formulation No. 2>the formulation No. 4>the formulation No. 3; the AUClast was ranked in descending order as the formulation No. 1>the formulation No. 3>the formulation No. 2>the formulation No. 4; the mean residence time MRTINF_obs was ranked in descending order as the formulation No. 3>the formulation No. 4>the formulation No. 2>the formulation No. 1; the distribution volume Vz_obs was ranked in descending order as the formulation No. 4>the formulation No. 3>the formulation No. 2>the formulation No. 1. It can be seen from the above comparison of the parameters that the formulation Nos. 2, 3 and 4 have longer MRT in vivo and larger distribution volume as compared to the formulation No. 1, suggesting that the in vivo sustained-release effect of the formulations of Examples 7-9 is significant.

TABLE 24

Pharmacokinetic parameters for 15 mg/kg fulvestrant suspensions of Examples 7-9 (formulation Nos. 2-4) and marketed comparative formulation intramuscularly injected into Wistar rats at a single dose

| | | Formulation No. 1 | | | | Formulation No. 2 | | | |
|---|---|---|---|---|---|---|---|---|---|
| Variables | Unit | N | Mean | SD | CV (%) | N | Mean | SD | CV (%) |
| AUClast | h*ng/mL | 6 | 5000 | 932 | 18.7 | 6 | 3490 | 745 | 21.3 |
| Cmax | ng/mL | 6 | 13.5 | 4.32 | 32.1 | 6 | 10.0 | 3.16 | 31.5 |
| MRT_obs | h | 6 | 641 | 136 | 21.3 | 6 | 1310 | 443 | 33.9 |
| MRTlast | h | 6 | 357 | 29.5 | 8.25 | 6 | 440 | 42.3 | 9.62 |
| *Tmax | h | 6 | 7.00 | 15.5 | 24.0 | 6 | 1.00 | 2.00 | 7.00 |
| Vz_F_obs | mL/kg | 6 | 1,450,000 | 421,000 | 29.1 | 6 | 2,470,000 | 881,000 | 35.6 |

| | | Formulation No. 3 | | | | Formulation No. 4 | | | |
|---|---|---|---|---|---|---|---|---|---|
| Variables | Unit | N | Mean | SD | CV (%) | N | Mean | SD | CV (%) |
| AUClast | h*ng/mL | 6 | 3970 | 701 | 17.6 | 6 | 3280 | 518 | 15.8 |
| Cmax | ng/mL | 6 | 8.10 | 2.89 | 35.7 | 6 | 9.23 | 2.78 | 30.1 |
| MRT_obs | h | 6 | 18,000 | 34,500 | 192 | 6 | 7820 | 13,300 | 170 |
| MRTlast | h | 6 | 518 | 13.6 | 2.63 | 6 | 505 | 36.7 | 7.26 |
| *Tmax | h | 6 | 1.00 | 3.00 | 3.00 | 6 | 1.00 | 1.00 | 1.00 |
| Vz_F_obs | mL/kg | 6 | 2,950,000 | 721,000 | 24.5 | 6 | 3,170,000 | 571,000 | 18.0 |

After 15 mg/kg formulation No. 3 (the fulvestrant formulation prepared in Example 8) was intramuscularly-injected into Wistar rats at a single dose, the Cmax of fulvestrant in plasma was 8.10±2.89 ng/mL, the area under the drug concentration-time curve AUCINF_obs was 71,800±125.000 h*ng/mL, AUClast was 3970±701 h*ng/mL, the drug's terminal elimination half-life T½_Z was 12,300±23,900 h, the clearance rate Cl_obs was 655±398 mL/h/kg, the mean residence time MRTINF_obs was 18.000±34,500 h, and the distribution volume Vz_obs was 2,950,000±721,000 mL/kg.

After 15 mg/kg formulation No. 4 (the fulvestrant formulation prepared in Example 9) was intramuscularly injected into Wistar rats at a single dose, the Cmax of fulvestrant in plasma was 9.23±2.78 ng/mL, the area under the drug concentration-time curve AUCINF_obs was 35,000±61,100 h*ng/mL, AUClast was 3280±518 h*ng/mL, the drug's Examples of the present disclosure have been described above. However, the present disclosure is not limited to the above examples. Any modification, equivalent, improvement and the like made without departing from the spirit and principle of the present disclosure shall fall within the protection scope of the present disclosure.

The invention claimed is:
1. A fulvestrant pharmaceutical composition comprising fulvestrant solid particles, a suspending agent, a wetting agent, an osmotic pressure regulator, a buffer, and a pH adjusting agent, wherein:
the fulvestrant solid particles have a particle size distribution having Dv(10) ranging from 0.600-2.000 μm, Dv(25) ranging from 1.000-3.000 μm, Dv(50) ranging from 0.800-4.000 μm, Dv(75) ranging from 1.000-4.000 μm, and Dv(90) ranging from 1.000-6.000 μm, provided that Dv(90) is not 1.000 μm, the particle size being determined using a laser particle analyzer with a dispersion medium: water, the refractive index of the dispersion medium: 1.333, the absorbance of the sample material: 0.01, and the refractive index of the sample material: 1.521;

the fulvestrant solid particles have a weight fraction of 10.00%-40.00%;

the suspending agent has a weight fraction of 0.20%-3.00% and is one or more selected from sodium carboxymethylcellulose, polyethylene glycol, and povidone;

the wetting agent has a weight fraction of 1.00%-3.00% and is one or more selected from poloxamer and tween; and the osmotic pressure regulator has a weight fraction of 1.00%-3.00% and is one or more selected from sodium chloride, mannitol, and sucrose.

2. The fulvestrant pharmaceutical composition according to claim 1, wherein the fulvestrant solid particles have a particle size distribution of Dv(10) ranging from 0.900-1.800 μm, Dv(25) ranging from 1.000-3.000 μm, Dv(50) ranging from 1.000-3.000 μm, Dv(75) ranging from 1.000-4.000 μm, Dv(90) ranging from 1.500-4.500 μm;

the suspending agent has a weight fraction of 0.20%-1.00% and is one or more selected from sodium carboxymethylcellulose, polyethylene glycol, and povidone;

the wetting agent has a weight fraction of 1.67%-1.74% and is one or more selected from poloxamer and tween; and the osmotic pressure regulator has a weight fraction of 2.29%-3.00% and is one or more selected from sodium chloride, mannitol and sucrose.

3. The fulvestrant pharmaceutical composition according to claim 1, further comprising a vehicle, wherein the vehicle is an oily vehicle and/or a non-oily vehicle;

the oily vehicle is selected from castor oil, triglyceride, cottonseed oil, and sesame oil; and the non-oily vehicle is water.

4. The fulvestrant pharmaceutical composition according to claim 1, further comprising one or more selected from a solvent, a stabilizer, a surfactant, a polymer, an electrolyte, a nonelectrolyte, and a co-solvent, wherein the polymer is a cross-linked polymer and/or a non-cross-linked polymer;

the solvent is one or more selected from water for injection and oil for injection;

the stabilizer is one or more selected from an antioxidant, a metal ion chelating agent, polyethylene oxide, polyethylene oxide derivatives, polysorbate, polyethoxylated vegetable oil, polyethoxylated castor oil, sorbitan palmitate, lecithin, polyvinyl alcohol, human serum albumin, polyvinylpyrrolidone calcium chloride, dextrose, glycerol, mannitol, and a cross-linked polymer;

the buffer is one or more selected from phosphoric acid, phosphate, citric acid, sodium citrate, hydrochloric acid, sodium hydroxide, sodium citrate, citric acid, tris(hydroxymethyl)aminomethane, and a mixture thereof;

the pH adjusting agent is one or more selected from phosphoric acid, phosphate, citric acid, sodium citrate, hydrochloric acid, and sodium hydroxide; and the co-solvent is one or more selected from ethanol and propylene glycol.

5. The fulvestrant pharmaceutical composition according to claim 4, wherein:

the antioxidant is one or more selected from citric acid, vitamin C, and vitamin E;

the metal ion chelating agent is ethylene diamine tetraacetic acid;

the poloxamer is one or more selected from poloxamer 188, poloxamer 124, and poloxamer 407;

the polysorbate is one or more selected from polysorbate 80 and polysorbate 20;

the povidone is one or more selected from povidone K12, povidone K17, povidone C-12, povidone C-17, and povidone C-30;

the polyethylene glycol is polyethylene glycol 3350;

the cross-linked polymer is sodium carboxymethylcellulose; and the phosphate is one or more selected from sodium dihydrogen phosphate monohydrate, sodium dihydrogen phosphate dihydrate, anhydrous sodium dihydrogen phosphate, disodium hydrogen phosphate monohydrate, disodium hydrogen phosphate dihydrate, and anhydrous disodium hydrogen phosphate.

6. The fulvestrant pharmaceutical composition according to claim 1, wherein the fulvestrant pharmaceutical composition is of formula III, formula IV, or formula V, wherein, formula III comprises 24.56 w/w % fulvestrant solid particles, 1.62 w/w % wetting agent, 1.00 w/w % suspending agent, 2.82 w/w % osmotic pressure regulator, 0.42 w/w % buffer, and 0-1 w/w % pH adjusting agent;

formula IV comprises 25.00 w/w % fulvestrant solid particles, 1.62 w/w % wetting agent, 1.00 w/w % suspending agent, 2.89 w/w % osmotic pressure regulator, 0.43 w/w % buffer, and 0-1 w/w % pH adjusting agent; and formula VI comprises 25.00 w/w % fulvestrant solid particles, 1.62 w/w % wetting agent, 0.20 w/w % suspending agent, 2.29 w/w % osmotic pressure regulator, 0.51 w/w % buffer, and 70.38 w/w % water.

7. The fulvestrant pharmaceutical composition according to claim 1, wherein the fulvestrant pharmaceutical composition is of formula C, formula D, or formula E, wherein, formula C comprises 24.66 w/w % fulvestrant solid particles, 1.62 w/w % tween 20, 1.00 w/w % sodium carboxymethylcellulose, 2.82 w/w % mannitol, 0.42 w/w % anhydrous sodium dihydrogen phosphate, sodium hydroxide, and sterile water for injection;

formula D comprises 25.00 w/w % fulvestrant solid particles, 1.62 w/w % tween 20, 1.00 w/w % sodium carboxymethylcellulose, 2.89 w/w % mannitol, 0.43 w/w % anhydrous sodium dihydrogen phosphate, sodium hydroxide, and sterile water for injection, wherein the fulvestrant pharmaceutical composition has a pH of 7.4; and formula E comprises 25.00 w/w % fulvestrant solid particles, 1.62 w/w % tween 20, 0.20 w/w % sodium carboxymethylcellulose, 2.29 w/w % mannitol, 0.09 w/w % anhydrous sodium dihydrogen phosphate, 0.42 w/w % anhydrous disodium hydrogen phosphate, and 70.38 w/w % sterile water for injection.

8. A pharmaceutical formulation comprising the fulvestrant pharmaceutical composition according to claim 1, wherein the fulvestrant pharmaceutical formulation is an injection; selected from a liquid injection, a powder for injection, and a tablet for injection, the liquid injection is selected from an aqueous suspension and an oily suspension, and the powder for injection is a freeze-dried powder injection.

9. The pharmaceutical formulation according to claim 8, wherein the injection is a long-acting injection, which is an aqueous suspension, an oily suspension, or a powder for suspension.

10. A method for treating hormone receptor-positive metastatic breast cancer, comprising administering the fulvestrant pharmaceutical formulation comprising the fulvestrant pharmaceutical composition according to claim 1 to a subject in need thereof.

\* \* \* \* \*